(12) United States Patent
Webber

(10) Patent No.: US 6,549,607 B1
(45) Date of Patent: Apr. 15, 2003

(54) METHOD AND SYSTEM FOR CREATING TASK-DEPENDENT THREE-DIMENSIONAL IMAGES

(75) Inventor: Richard L. Webber, Clemmons, NC (US)

(73) Assignee: Wake Forest University, Winston-Salem, NC (US)

(*) Notice: Subject to any disclaimer, the term of this patent is extended or adjusted under 35 U.S.C. 154(b) by 0 days.

(21) Appl. No.: 09/561,376

(22) Filed: Apr. 28, 2000

Related U.S. Application Data

(63) Continuation-in-part of application No. 09/252,632, filed on Feb. 19, 1999, now Pat. No. 6,081,577.
(60) Provisional application No. 60/095,463, filed on Jul. 24, 1998.

(51) Int. Cl.⁷ .................................................. A61B 6/03
(52) U.S. Cl. .............................. 378/8; 378/21; 378/94
(58) Field of Search ........................... 378/4, 8, 19, 21, 378/22, 94

(56) References Cited

U.S. PATENT DOCUMENTS

| | | | |
|---|---|---|---|
| 4,662,379 A | | 5/1987 | Macovski |
| 4,920,491 A | * | 4/1990 | Eberhard et al. ........... 378/901 |
| 4,941,164 A | | 7/1990 | Schuller |
| 5,008,947 A | | 4/1991 | Yamada |
| 5,051,904 A | | 9/1991 | Griffith |
| 5,070,454 A | | 12/1991 | Griffith |
| 5,299,254 A | | 3/1994 | Dancer et al. |
| 5,319,550 A | | 6/1994 | Griffith |
| 5,359,637 A | | 10/1994 | Webber |
| 5,642,293 A | | 6/1997 | Manthey et al. |
| 5,668,844 A | | 9/1997 | Webber |
| 5,751,787 A | * | 5/1998 | Jing et al. ................... 378/169 |
| 5,755,725 A | | 5/1998 | Druais |
| 5,828,722 A | | 10/1998 | Ploetz et al. |
| 5,872,828 A | | 2/1999 | Niklason |
| 5,878,104 A | | 3/1999 | Ploetz |
| 6,081,577 A | | 6/2000 | Webber |

(List continued on next page.)

FOREIGN PATENT DOCUMENTS

| | | |
|---|---|---|
| GB | 2016855 | 9/1979 |
| WO | WO 93 22893 | 11/1993 |

OTHER PUBLICATIONS

EVS–125 X–Ray Slicer catalog, Unihaito Co., Ltd. Shinjuku–ku, Tokyo, no date.

Tsueno Saieto et al., "Three–Dimensional Quantitve Coronary Angiography", IEEE Transactions on Biomedical Engineering, vol. 37, No. 8, Aug. 1990, pp. 768–777.

(List continued on next page.)

Primary Examiner—David V. Bruce
(74) Attorney, Agent, or Firm—Dann, Dorfman, Herrell and Skillman

(57) ABSTRACT

A system and method for producing three-dimensional representations of an object. A first series of projected images of the selected object is recorded in a first projection plane and a second series of projected images of the selected object is recorded in a second projection plane. The first and the second series of projected images are rendered at a common magnification. The first set of projected images is then integrated into a first three-dimensional volume and the second set of projected images is integrated into a second three-dimensional volume. The three-dimensional representation of the object is then produced by combining one projected image from the first set of projected images with one projected image from the second set of projected images. Alternatively, the three-dimensional representation is produced by merging the first three-dimensional volume with the second three-dimensional volume.

6 Claims, 35 Drawing Sheets

U.S. PATENT DOCUMENTS

| | | | |
|---|---|---|---|
| 6,118,845 A | 6/2000 | Simon et al. | |
| 6,120,180 A | 9/2000 | Graumann | |
| 6,122,541 A | 9/2000 | Cosman et al. | |
| 6,158,888 A | * 12/2000 | Walker et al. | 378/169 |
| 6,249,568 B1 | 9/2001 | Rizo et al. | |
| 6,289,235 B1 | 9/2001 | Webber et al. | |

OTHER PUBLICATIONS

"Proceedings of the 14$^{th}$ Annual Meeting of the American Association of Physicists", vol. 17, No. 6, Jun. 26–29, 1972, Philadelphia, p 878 R. Mohan et al. "A Computer–Assisted Rapid Method for Source Localization in Interstitial Implants" abstract.

Webber et al. "Synthesis of Arbitrary x–Ray Projections From A Finite Number of Existing Projections", SPIE, vol. 535, 1985, p. 84–91.

Grant, D.G., Tomosynthesis: A Three–Dimensional Radiographic Imaging Technique, IEEE Transactions on Bio–Medical Engineering, vol. BME–19, No. 1, Jan. 1972, pp. 20–28.

Ruttimann, U.E. et al. An Optimal Synthetic aperture for circular Tomosynthesis, Medical Physics, vol. 16, No. 3, May/Jun. 1989, pp. 398–405.

Webber et al., Tunedaperture computed tomography (TACT™). Theory and application for three–dimensionsl dento–alveolar imaging, Dentomaxillofacial Radiology (1997) 26, pp. 53–62.

Ruttimann, U.E., et al., Restoration of Digital Multiplane Tomosynthesis by a Constrained Iteration Method, IEEE Transactions on Medical Imaging, vo. ME–3, No. 3, Sep. 1984, pp. 141–148.

* cited by examiner

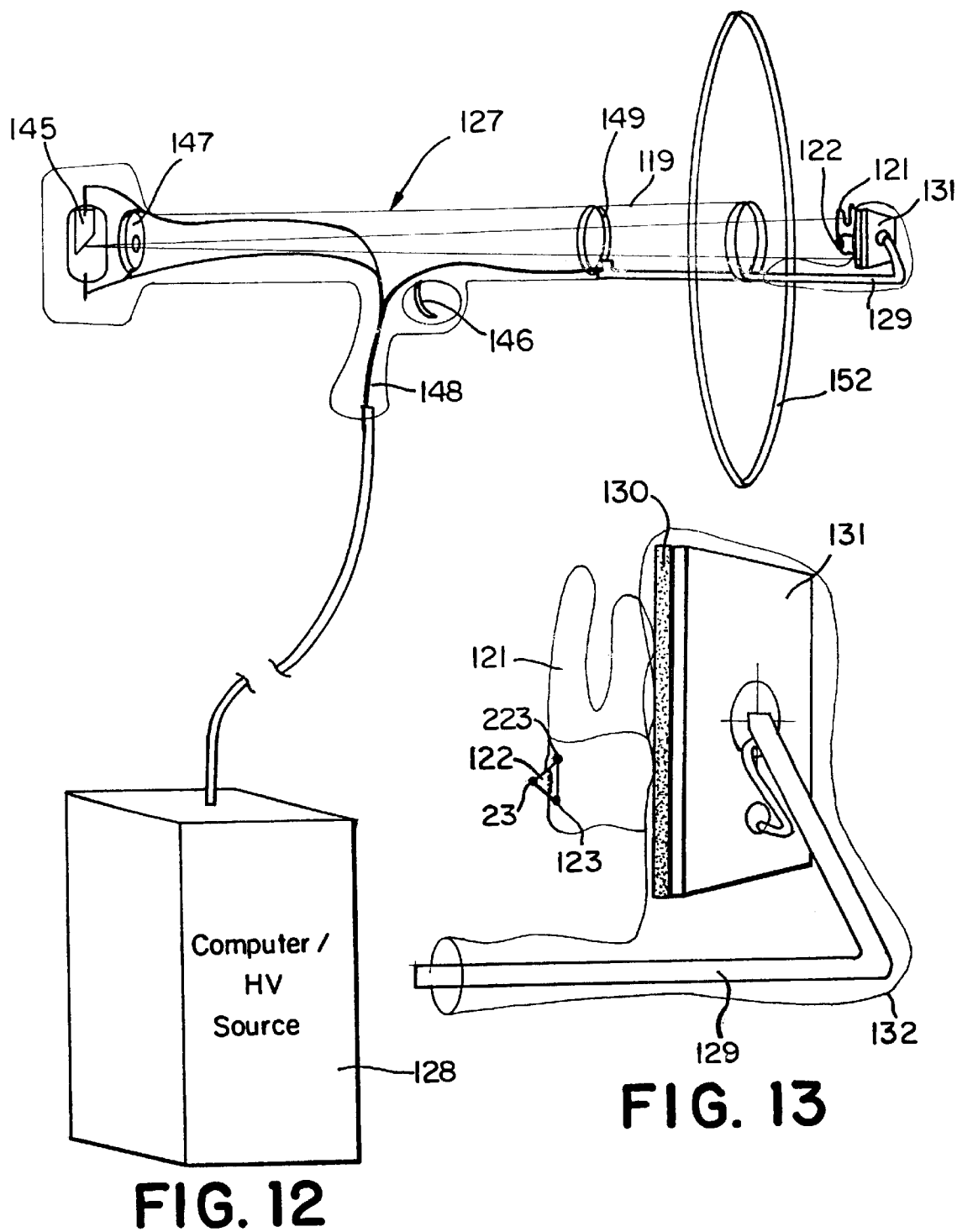

1120 — RECORD INDEPENDENT SETS OF ORTHOGONALLY ORIENTED IMAGE SLICES.

1122 — INTEGRATE EACH SET OF IMAGE SLICES INTO A 3-D MATRIX VOLUME.

1124 — AFFINIZATION OF EACH 3-D MATRIX VOLUME.

1126 — ROTATION OF AFFINE MATRIX VOLUME.

1128 — MERGE MATRIX VOLUMES.

FIG. 29
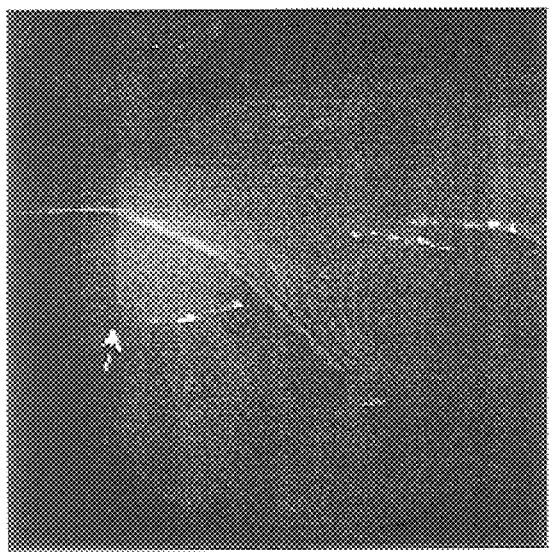
FIG. 30
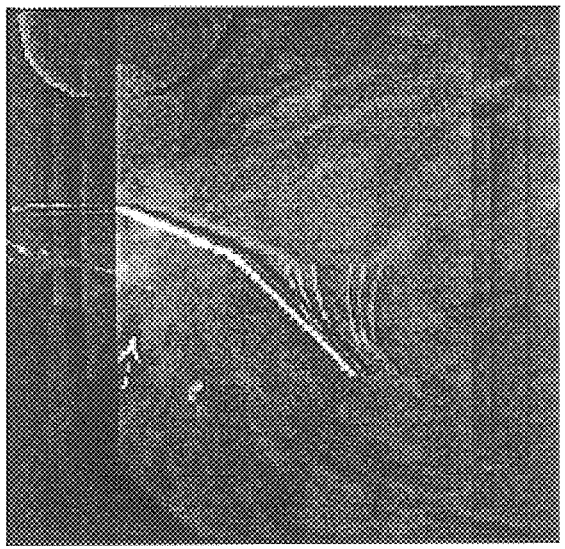
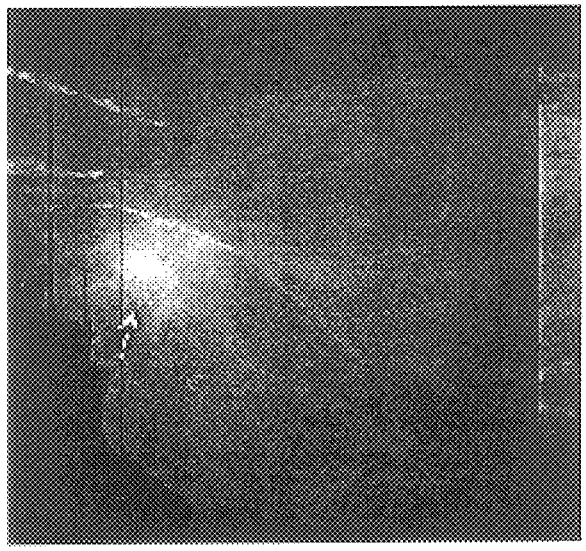
FIG. 31

METHOD AND SYSTEM FOR CREATING TASK-DEPENDENT THREE-DIMENSIONAL IMAGES

RELATED APPLICATIONS

This application is a continuation-in-part of application Ser. No. 09/252,632, entitled "Method And System For Creating Task-Dependent Three-Dimensional Images," filed on Feb. 19, 1999, now U.S. Pat. No. 6,081,577 such application being incorporated herein by reference, and which in turn claims the benefit of U.S. provisional patent application Serial No. 60/095,463, entitled "Non-Linear Algorithm for Task-Specific Tomosynthetic Image Reconstruction," filed on Jul. 24, 1998.

FIELD OF THE INVENTION

The present invention relates to a method and system for creating three-dimensional displays or images from a multiplicity of two-dimensional projected images and, more specifically, to a method and system for producing task-dependent radiographic images of an object of interest which are substantially free of blurring artifacts.

BACKGROUND OF THE INVENTION

A variety of three-dimensional imaging modalities has been developed for medical applications, as well as for use in non-destructive testing of manufactured parts. In particular, a wide range of tomosynthetic imaging techniques has previously been demonstrated to be useful in examining three-dimensional objects by means of radiation. These imaging techniques differ in the size and configuration of the effective imaging aperture. At one extreme, the imaging aperture approaches zero (i.e., a pinhole) and the resulting display is characterized by images produced from a single transmission radiograph. This yields an infinitely wide depth of field and therefore no depth information can be extracted from the image. At the other extreme, the aperture approaches a surrounding ring delimiting an infinite numerical aperture resulting in projection angles orthogonal to the long axis of the irradiated object. This yields an infinitely narrow depth of field and hence no information about adjacent slices through the object can be ascertained. It therefore follows that a "middle ground" approach, which provides the ability to adapt a sampling aperture to a particular task, would be highly advantageous.

The key to achieving the full potential of diagnostic flexibility lies in the fact that perceptually meaningful three-dimensional reconstructions can be produced from optical systems having any number of different aperture functions. That fact can be exploited since any aperture can be approximated by summation of a finite number of appropriately distributed point apertures. The key is to map all incrementally obtained projective data into a single three-dimensional matrix. To accomplish this goal, one needs to ascertain all positional degrees of freedom existing between the object of interest, the source of radiation, and the detector.

In the past, the relative positions of the object, the source, and the detector have been determined by fixing the position of the object relative to the detector while the source of radiation is moved along a predetermined path, i.e. a path of known or fixed geometry. Projective images of the object are then recorded at known positions of the source of radiation. In this way, the relative positions of the source of radiation, the object of interest, and the detector can be determined for each recorded image.

A method and system which enables the source of radiation to be decoupled from the object of interest and the detector has been described in U.S. Pat. No. 5,359,637, that issued on Oct. 25, 1994, which is incorporated herein by reference. This is accomplished by fixing the position of the object of interest relative to the detector and providing a fiducial reference which is in a fixed position relative to the coupled detector and object. The position of the image of the fiducial reference in the recorded image then can be used to determine the position of the source of radiation. In addition, a technique for solving the most general application wherein the radiation source, the object of interest, and the detector are independently positioned for each projection has been described by us in co-pending U.S. patent application Ser. No. 09/034,922, filed on Mar. 5, 1998, which is also incorporated herein by reference.

Once the relative positions of the radiation source, the object, and the detector are determined, each incrementally obtained projective image is mapped into a single three-dimensional matrix. The mapping is performed by laterally shifting and summing the projective images to yield tomographic images at a selected slice position through the object of interest. A three-dimensional representation of the object can be obtained by repeating the mapping process for a series of slice positions through the object. However, the quality and independence of the tomographic images is compromised by blurring artifacts produced from unregistered details located outside the plane of reconstruction.

In addition, quantitative information has traditionally been difficult to determine from conventional tomography. Although many questions of medical interest are concerned with temporal changes of a structure (e.g., changes in the size and shape of a tumor over time), the ability to compare diagnostic measurements made over time is complicated by the fact that factors other than the parameter of diagnostic interest often contribute to the measured differences. For example, spatial variations produced from arbitrary changes in the observational vantage point(s) of the radiation source create differences between the measurements which are unrelated to temporal changes of the object being investigated. In addition, conventional X-ray sources produce radiation that varies with changes in tube potential, beam filtration, beam orientation, tube current, distance form the focal spot, and exposure time. The fluctuations in the output of radiation sources is therefore another factor that limits the ability to derive quantitative information from conventional tomography.

In light of the foregoing, it would be highly beneficial to provide a method for producing a three-dimensional representation of an object that is substantially free of blurring artifacts from unregistered details. In addition, the method should enable quantitative information related to temporal changes associated with the object to be measured.

SUMMARY OF THE INVENTION

The present invention relates to a system and a method for synthesizing an image slice through a selected object from a plurality of projected radiographic images of the selected object. The system comprises a radiation source for irradiating the object. The preferred radiation source depends upon the particular application. For example, the present invention may be practiced using x-rays, electron microscopy, ultrasound, visible light, infrared light, ultraviolet light, microwaves, or virtual radiation simulated by manipulation of magnetic fields (magnetic resonance imaging (MRI)). In one embodiment of the present invention, the position of the radiation source within a plane parallel to an image plane is determined from projected images of two object points associated with a fiducial reference which is maintained in fixed position relative to the selected object. Once the projected images are compensated for differences in magnification, the relative position of the radiation source within the plane parallel to the image plane is determined from an estimate of the actual distance between the two object points obtained from a sinusoidal fit of the distances between the projected images of the object points.

A recording medium or radiation detector is used to record a series of projected images of the selected object. The recording medium may be in the form of a photographic plate or a radiation-sensitive, solid-state image detector such as a charge-coupled device (CCD), or any other system capable of producing two-dimensional projections or images suitable for digitization or other analysis.

An image synthesizer is provided for transforming the series of projected images of the selected object into an image slice. The image slice consists of an array of pixels with each pixel having an associated attenuation value and corresponds to a cross-sectional slice through the selected object at a selected slice position. A three-dimensional representation of the object can be obtained by repeating the transformation at a series of slice positions through the object.

In addition, an optional source comparator is provided for adjusting the radiation source to enable meaningful quantitative comparisons between projected images recorded either at different times and/or using different radiation sources. The source comparator is positionable between the radiation source and the radiographic medium for producing a gradient image indicative of characteristics associated with the output from the radiation source. In operation, the source comparator is used to record a first gradient image using a first radiation source at the same time that a first projected image or series of projected images is recorded. When a second projected image or series of projected images are to be recorded, the source comparator is used to record a second gradient image. The second gradient image is compared to the first gradient and differences between the two gradient images are noted. The beam energy, filtration, and beam exposure associated with the radiation source used to record the second gradient image are then adjusted to minimize the differences between the first gradient image and the second gradient image.

In one embodiment, the source comparator comprises two wedges or five-sided polyhedrons of equal dimension having a rectangular base and two right-triangular faces. The triangular faces lie in parallel planes at opposite edges of the base such that the triangular faces are oriented as mirror images of each other. As a result, each wedge has a tapered edge and provides a uniformly increasing thickness from the tapered edge in a direction parallel to the plane of the base and perpendicular to the tapered edge. The wedges are arranged with the base of one wedge adjacent to the base of the other wedge such that the tapered edges of the two wedges are at adjacent edges of the base. One wedge is formed from a uniform high attenuation material while the other wedge is formed from a uniform low attenuation material. Accordingly, when the source comparator is irradiated from a radiation source directed perpendicularly to the bases of the wedges, the resulting image will be a quadrilateral having an intensity gradient that is maximized in a particular direction.

In operation, the system of the present invention is used to produce an image slice through the selected object that is substantially free of blurring artifacts from unregistered details located outside a plane of reconstruction. The radiation source and recording medium are used to record a series of two-dimensional projected images of the selected object. The series of two-dimensional projected images are then shifted by an amount and in a direction required to superimpose the object images of the two-dimensional images. The shifted two-dimensional images can then be combined in a non-linear manner to generate a tomosynthetic slice through the selected object. In one embodiment, the two-dimensional images are combined by selecting details from a single projection demonstrating the most relative attenuation at each pixel. Alternatively, a different non-linear operator could be used wherein the two-dimensional images are combined by selecting details from a single projection demonstrating the least relative attenuation at each pixel in the reconstructed image. Optionally, a series of reconstructed images at varying slice positions through the selected object are determined to create a three-dimensional representation of the selected object.

Alternatively, the system of the present invention is used to synthesize a three-dimensional reconstruction of the object from as few as two projected images of the object. A first projected image of the object is recorded in a first projection plane and a second projected image is recorded in a second projection plane. Each of the first and the second projected images are then rendered at a common magnification. Using a known angle between the first and the second projection planes, the first and the second projected images are transformed to occupy the same volume. The transformed first and second projected images are then combined into a three-dimensional representation of the selected object. Additional projected images are optionally combined with the three-dimensional representation to refine the three-dimensional representation.

In yet another embodiment, the system of the present invention is used to synthesize a three-dimensional representation of the selected object from two or more sets of projected images of the selected object. The first and second sets of projected images are tomosynthetically transformed into a series of contiguous slices forming a first and a second three-dimensional volume, respectively, using previously disclosed methods (e.g., U.S. Pat. No. 5,668,844) or those in the public domain (e.g., tomosynthesis). The first and second three-dimensional volumes are then rendered at a common magnification. The second three-dimensional volume is then rotated by an angle corresponding to the angular disparity between the first and the second three-dimensional volumes. The rotated second three-dimensional volume is then merged with the first three-dimensional volume to produce a three-dimensional representation of the selected object.

Alternatively, the system of the present invention can be used to determine temporal changes in the selected object. The radiation source and recording medium are used to record a first series of two-dimensional projected images of the selected object. At some later time, the radiation source and recording medium are used to record a second series of two-dimensional projected images of the selected object. Both series are tomosynthetically converted into a series of slices via previously disclosed methods (TACT®) or those in the public domain (tomosynthesis). Each slice of the first series is then correlated with a corresponding slice of the second series to form pairs of correlated slices. Each pair of slices is then aligned to maximize the overlap between homologous structures. Each pair of correlated slices is then subtracted to produce a difference image. Each difference image is then displayed individually. Alternatively, all of the difference images can be overlapped to yield a complete difference image corresponding to the volumetric difference associated with the entire tomosynthetically reconstructed volume.

When a three-dimensional representation of the selected object is produced, the three-dimensional representation can be viewed holographically using a display in accordance with the present invention. The display comprises stereoscopic spectacles which are worn by an observer and a target operatively associated with the spectacles. Accordingly, as the observer changes his or her vantage point, movement of the spectacles translates into a corresponding movement of the target. A detector is operatively associated with the target for tracking movement of the target. The detector is connected to a monitor such that the monitor receives a signal from the detector indicative of movement of the target. In response to the signal from the detector, the monitor displays an image pair of the three-dimensional representation which, when viewed through the spectacles produces a stereoscopic effect. The image pair which is displayed is changed to compensate for changes in the vantage point of the observer.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 12 is a schematic representation of an embodiment of the present invention wherein the source is a hand-held X-ray source which is constrained relative to the recording medium by a C-arm;

FIG. 13 is an enlarged schematic representation of the object of interest and the recording medium depicted in FIG. 14;

FIG. 29 is a tomosynthetic slice through a human breast reconstructed using a linear summation of projected images;

FIG. 30 is a tomosynthetic slice through the human breast reconstructed using a linear summation of projected images augmented by a deconvolution filter; and FIG. 31 is a tomosynthetic slice through the human breast reconstructed using a non-linear reconstruction scheme;

DETAILED DESCRIPTION OF THE PREFERRED EMBODIMENTS

Figure 1:
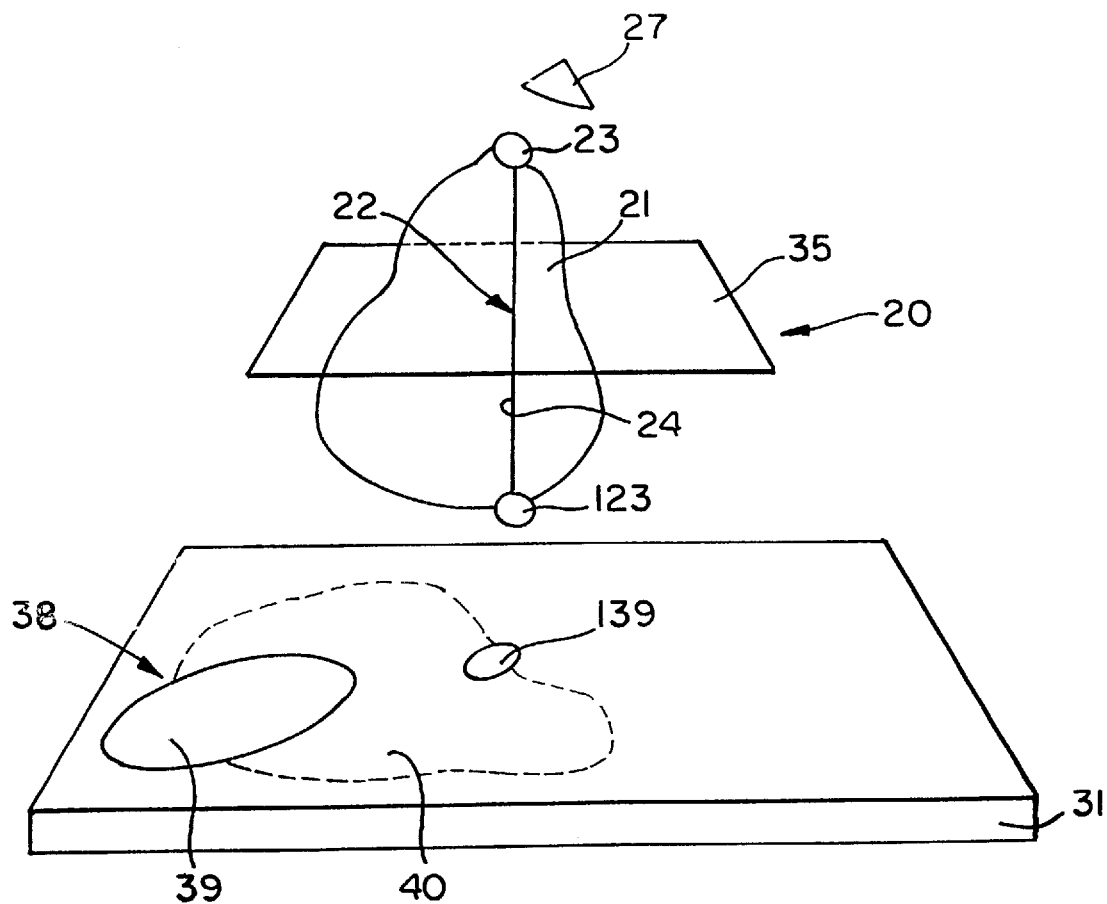
FIG. 1 is a schematic representation of a system for creating three-dimensional radiographic displays using computed tomography in accordance with the present invention.
Figure 38:
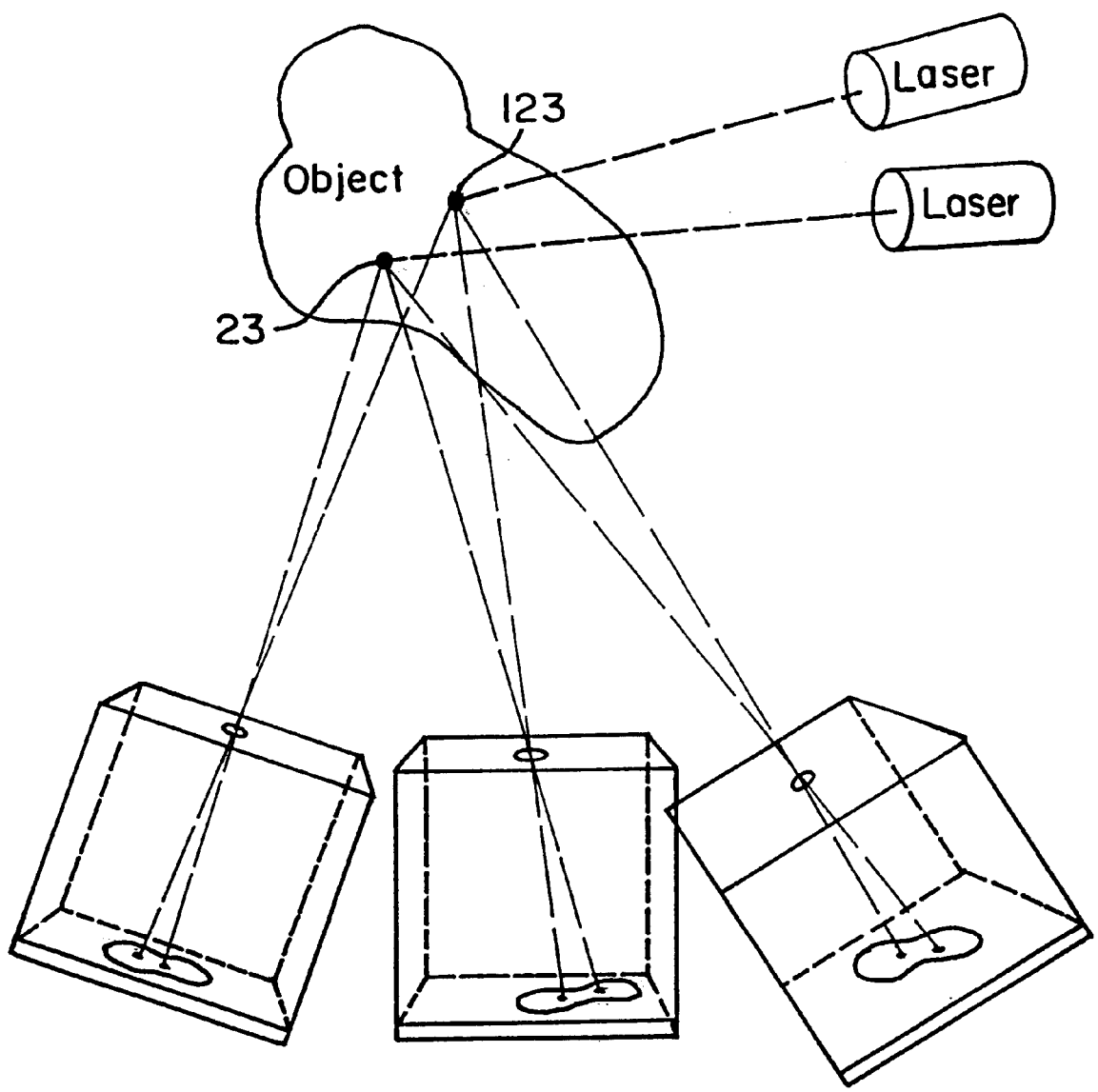
FIG. 38 is a schematic representation of an embodiment of the present invention wherein laser light sources provide fiducial reference points.

The present invention generally relates to a system 20, as depicted schematically in FIG. 1, for synthesizing an image of an object 21 at a selected slice position 35 through the object 21 from a plurality of radiographic projected images 38 of the selected object 21. A fiducial reference 22 is held in a fixed position relative to the selected object 21, for example, by directly attaching the fiducial reference 22 to the object 21. The fiducial reference comprises two finite sized, identifiable reference markers, 23 and 123, which are maintained coupled together in a fixed geometry relative to each other by a radiolucent bar 24. However, the fiducial reference 22 may comprise various numbers and arrangements of reference markers 23. Alternatively, as shown in FIG. 38, the reference markers, 23 and 123, are provided by the reflection of laser light from the surface of the selected object. A radiation source 27 is provided to irradiate the object 21 along with the fiducial reference 22. Irradiation of the object 21 casts a projected image 38 onto a recording medium 31. The projected image 38 comprises an object image 40 of the object 21 and reference images, 39 and 139, of the reference markers, 23 and 123, respectively.

In general, the pattern of source 27 positions does not need to be in any fixed geometry or position. Indeed, the position of the source 27 may be totally arbitrary in translation and displacement relative to the object 21. Likewise, the recording medium 31 may also be arbitrarily movable relative to the object 21 by translation, displacement, tilting, or rotation. The only requirement is that for every degree of freedom in the system resulting from movement of the source 27 or the recording medium 31 relative to the object 21, the fiducial reference 22 must include sufficient measurable or defined characteristics, such as size, shape, or numbers of reference markers 23, to account for each degree of freedom.

The minimum number of reference markers required to completely determine the system depends on the constraints, if any, imposed on the relative positions of (1) the radiation source, (2) the object and fiducial reference, and (3) the recording medium. The system may have a total of nine possible relative motions (2 translations and 1 displacement for the radiation source relative to a desired projection plane and 2 translations, 1 displacement, 2 tilts, and 1 rotation for the recording medium relative to the desired projection plane). Each of these possible relative motions must be capable of analysis either by constraining the system and directly measuring the quantity, by providing a sufficient number of reference markers to enable the quantity to be determined, or by estimating the value of the quantity. Each unconstrained relative motion represents a degree of freedom for the system. For a system to be completely determined, the total number of degrees of freedom in the system must be less than or equal to the total number of degrees of freedom associated with the fiducial reference.

More than the minimum number of reference markers can be used. In such cases, the system is overdetermined and least squares fitting can be used to improve the accuracy of the resulting image slices. If, however, less than the minimum number of reference markers is used, then the system is underdetermined and the unknown degrees of freedom must either be estimated or measured directly.

Although the reference markers can be essentially any size and shape, spherical reference markers of known diameter may be used. When using spherical reference markers of a finite size, a single reference marker can account for up to five degrees of freedom. When a spherical reference marker is projected obliquely onto the recording medium, the reference image cast by the spherical reference marker is elliptical and is independent of any rotation of the reference marker. Determining the position of the reference image in the projection plane (X- and Y-coordinates) and the magnitudes of the major and minor diameters of the elliptical image accounts for four degrees of freedom. Further, when the distance between the radiation source and the reference marker is sufficiently short, the reference image will be magnified relative to the actual size of the reference marker, thereby accounting for an additional degree of freedom. In contrast, only two degrees of freedom (the X- and Y-coordinates) are typically associated with the reference image of a point-size reference marker.

Figure 4:
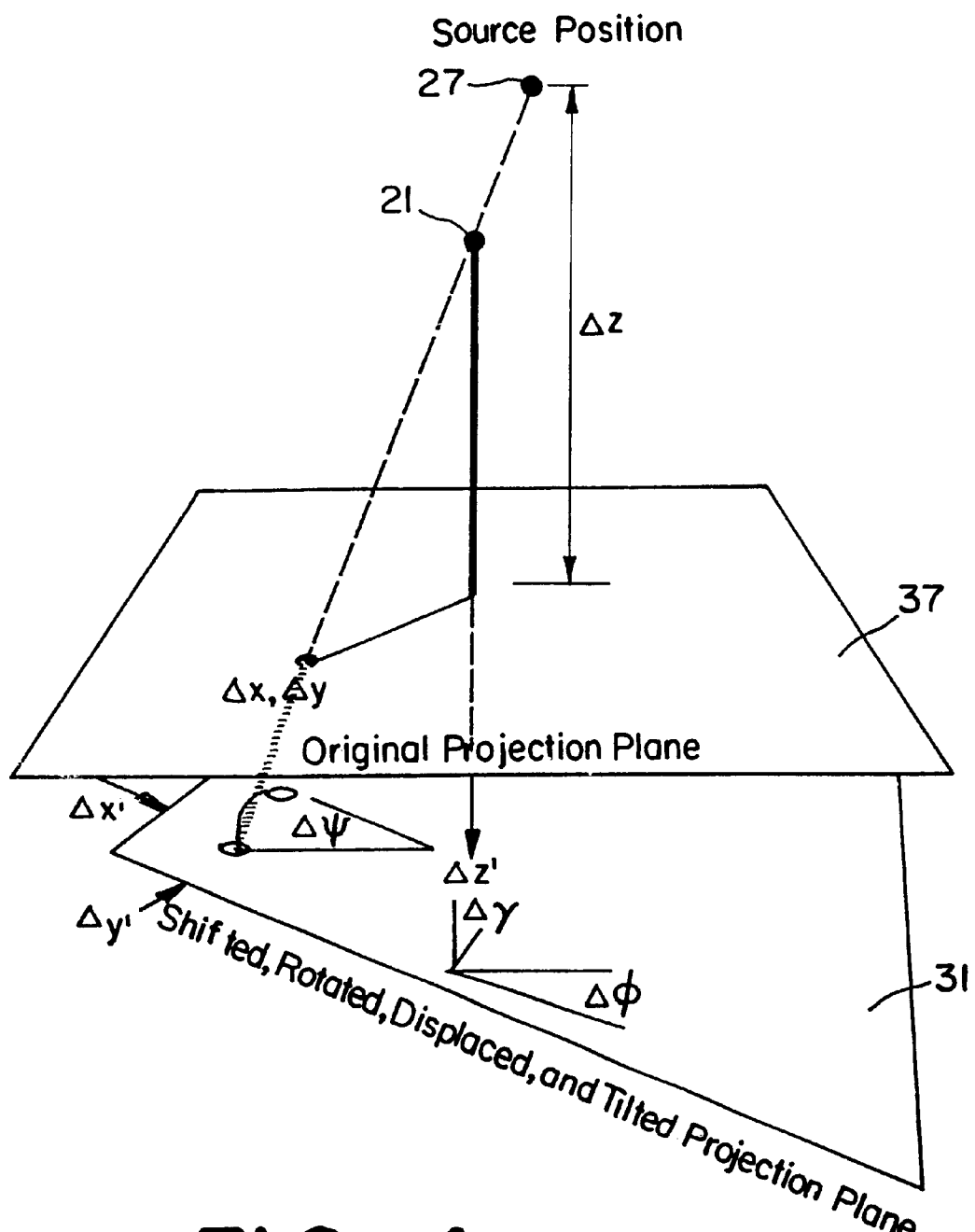
FIG. 4 is a schematic representation of a system having nine degrees of freedom in which a source is shifted and displaced relative to an original projection plane and in which a projection plane of a recording medium is shifted, rotated, displaced, and tilted relative to the original projection plane.

The most complex, yet most generally applicable, arrangement is depicted in FIG. 4, wherein the radiation source 27 and the recording medium 31 are completely unconstrained and uncoupled from the selected object 21. In this arrangement, there are nine degrees of freedom: 2 translational ($\Delta X$ and $\Delta Y$) and 1 displacement ($\Delta Z$) degrees of freedom for the radiation source 27 relative to an original or desired projection plane 37 and 2 translational ($\Delta X'$ and $\Delta Y'$), 1 displacement ($\Delta Z'$), 2 tilting ($\Delta \gamma$ and $\Delta \Phi$), and 1 rotational ($\Delta \Psi$) degree of freedom for the recording medium 31 relative to the original or desired projection plane. Accordingly, a fiducial reference system sufficient to solve a projection system having nine degrees of freedom is needed to completely determine the system.

One embodiment of the present invention that permits this general arrangement to be realized conveniently involves two-dimensional projected images from a system comprised of a fiducial reference having five point-size or finite reference markers.

Figure 5:
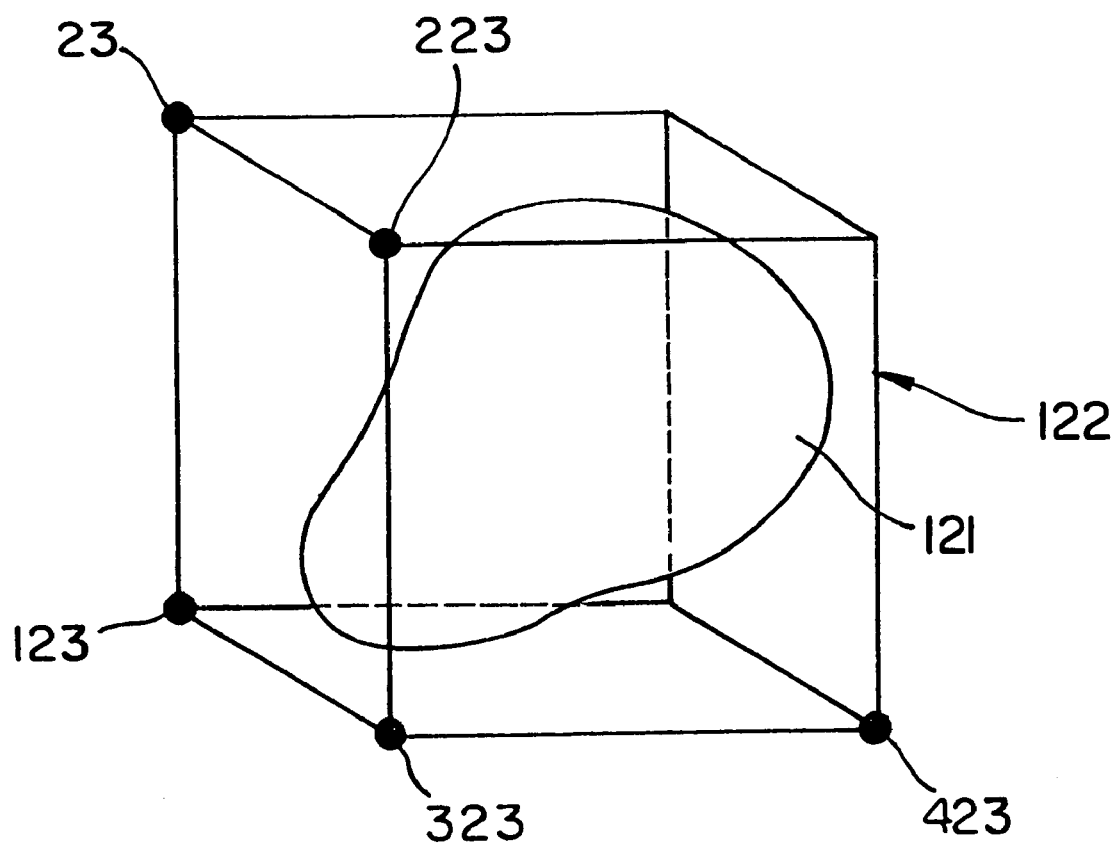
FIG. 5 is a schematic representation showing an arrangement of reference markers in accordance with the an embodiment of the present invention, wherein five spherical reference markers are positioned at five of the eight vertices of a cube.

This approach conveniently facilitates three-dimensional reconstructions when exactly four reference markers are coplanar and no three or more reference markers are collinear. Under these conditions, only the projection from the non-coplanar marker need be distinguished from the other four because the projections from the latter always bear a fixed sequential angular arrangement relative to each other which simplifies identification of homologous points in all projections. For example, the reference markers can be placed at five contiguous vertices of a cube as shown in FIG. 5. Fiducial reference 122 comprises five reference markers, 23, 123, 223, 323, 423, positioned contiguously at five vertices of a cube. The object 121 is preferably positioned within the cube. The four co-planar reference markers, 23, 123, 223, and 323, then can be used for projectively warping or transforming the projected images onto a desired projection plane while the remaining reference marker 423 serves as the alignment marker required to determine the normalized projection angle as described in U.S. Pat. No. 5,359,637.

The most general reconstruction task requiring information sufficient to determine all nine possible degrees of freedom requires computation of separate projective transformations for each projected image in each and every slice. However, by limiting the region of interest to a subvolume constrained such that the magnification across and between its slices may be considered constant, it is possible to generate veridical three-dimensional images within the volume much more efficiently. The increase in efficiency under these conditions results from the fact that all projections within this region can be mapped by a single fixed transformation, and that associated slice generation can be accomplished by simple tomosynthetic averaging of laterally shifted projections as described in U.S. Pat. No. 5,359,637.

Figure 11:
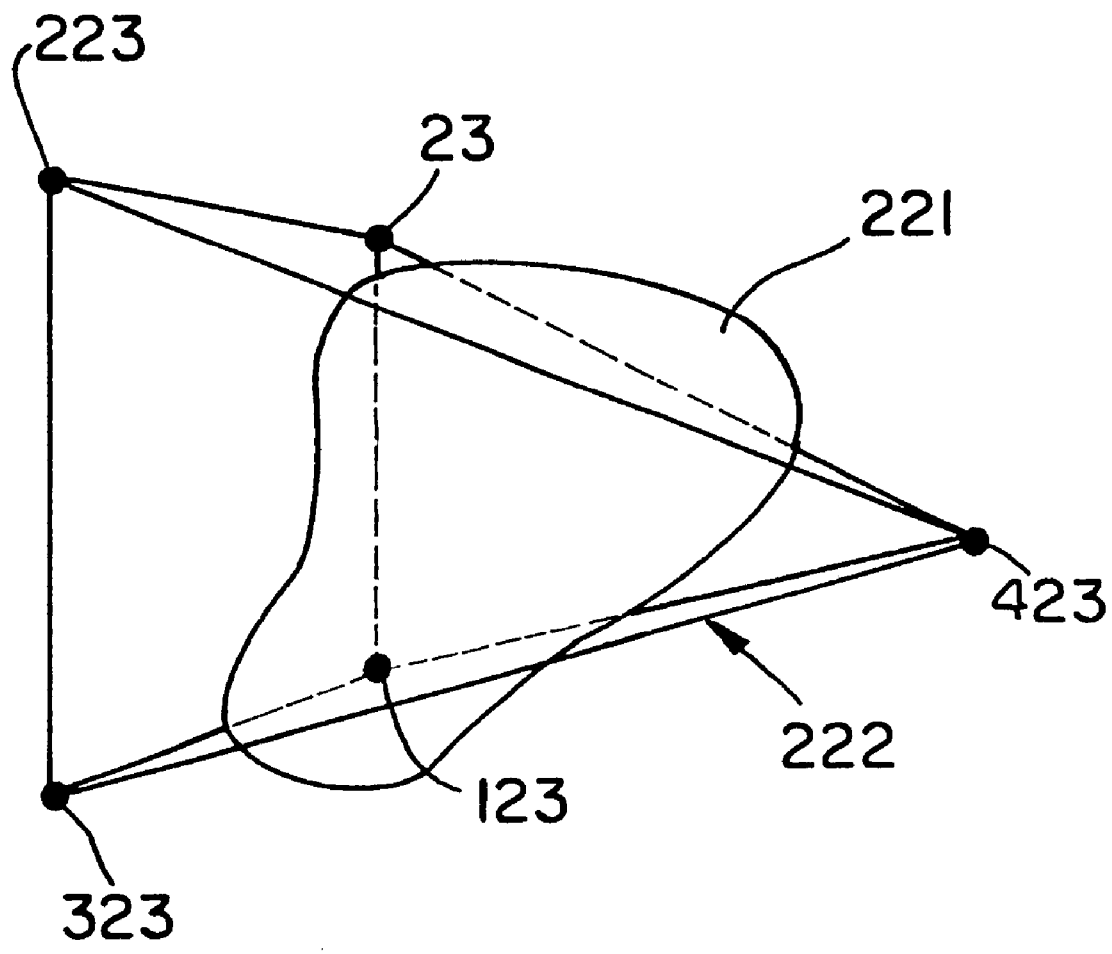
FIG. 11 is a schematic representation of an embodiment of the present invention wherein the reference markers of the fiducial reference are positioned at the vertices of a square pyramid.

Another useful arrangement of the fiducial reference comprising five reference markers is shown in FIG. 11, wherein a fiducial reference 222 employing a pyramidal distribution of reference markers 323 is used. The fiducial reference 222 comprises five reference markers 23, 123, 223, 323, and 423, which are held in a fixed relationship relative to each other and to the object 221. As was the case in FIG. 5, four of the reference markers, 23, 123, 223, and 323, lie in a plane that can be used to establish the desired projection plane. Here, they define the four corners of the base of a pyramid. The fifth reference marker 423 is positioned to define the apex of the pyramid and serves as the means for determining the projection angles relative to the desired projection plane as described in U.S. Pat. No. 5,359,637. In use, the fiducial reference 222 may be attached or fixed relative to the object 221 such that the base of the pyramid is proximate to the recording medium and the apex of the pyramid is proximate to the source.

Figure 15:
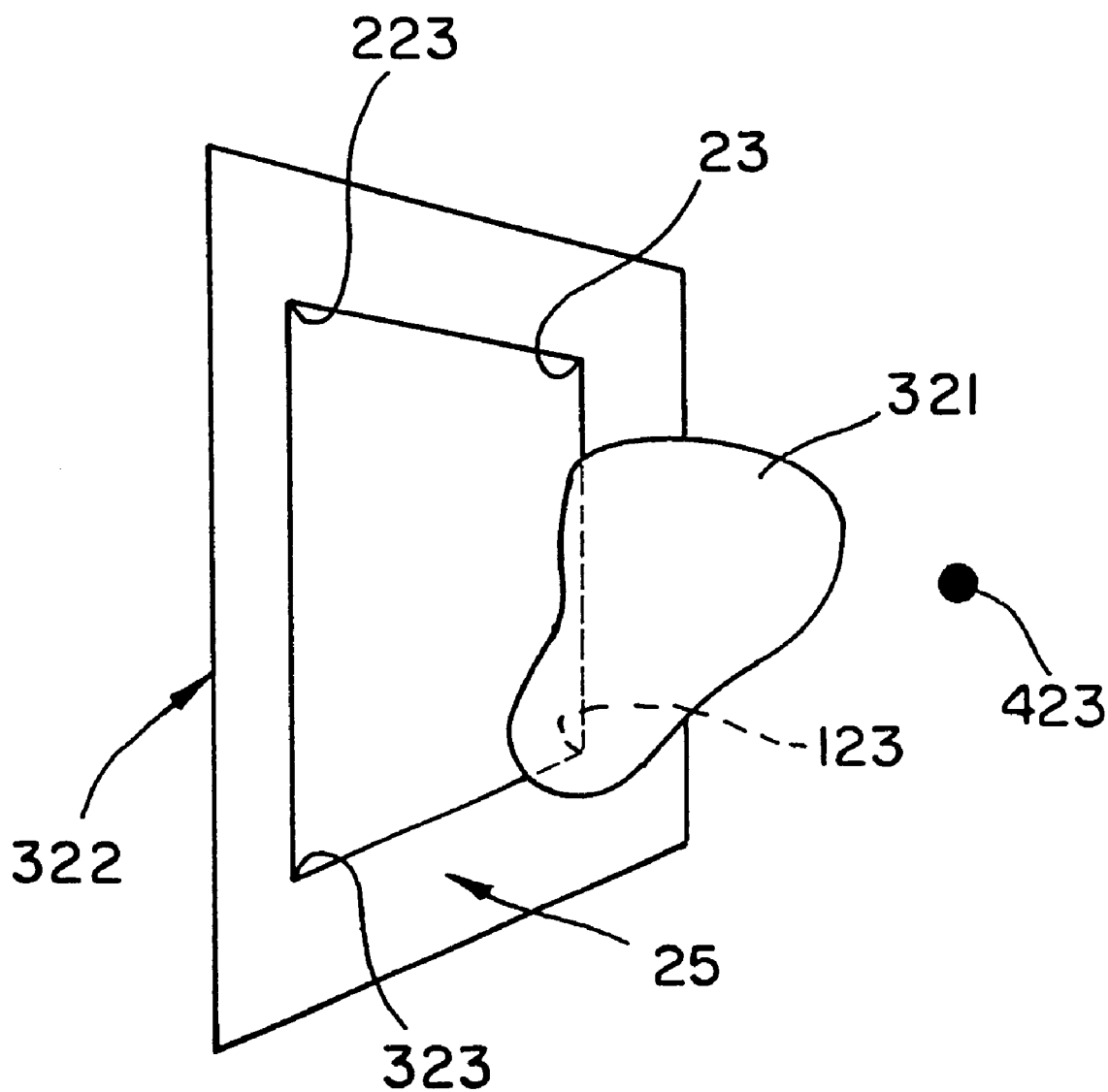
FIG. 15 is a schematic representation of an embodiment of the present invention wherein the corners of a frame define four reference markers.

In FIG. 15, a fiducial reference 322 having an alternative arrangement of reference markers in a pyramidal distribution is shown. In this arrangement, the fiducial reference 322 comprises a radiopaque frame 25 having a radiolucent central window. The four inside corners of the radiopaque frame 25 define four reference markers, 23, 123, 223, and 323, at the base of the pyramid. The fifth reference marker 423 is positioned at the apex of the pyramid. Preferably, the object 321 is positioned between the frame 25 and the reference marker 423.

Figure 14:
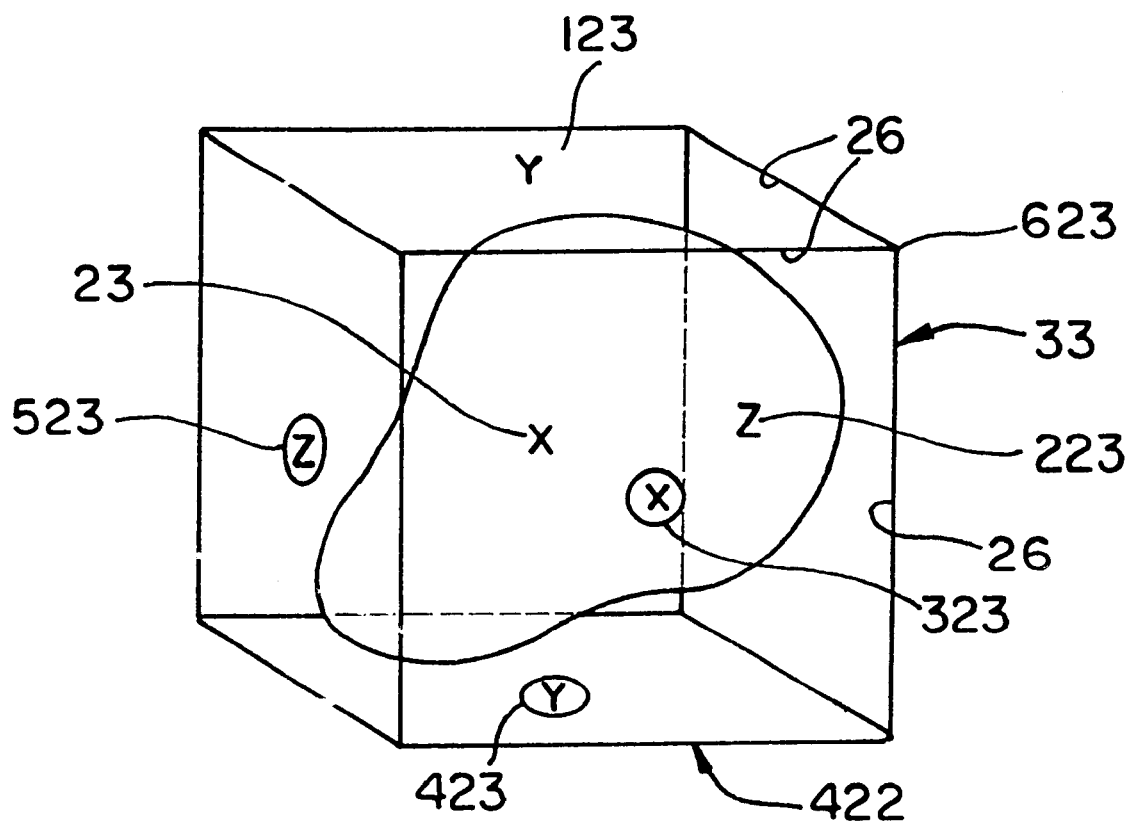
FIG. 14 is a schematic representation of an embodiment of the present invention wherein the reference markers of the fiducial reference are positioned at the centers of the faces of a parallelpiped.

In FIG. 14, a fiducial reference 422 which is also useful for solving a system with nine degrees of freedom is shown. Fiducial reference 422 comprises a rectangular parallelpiped 33 with radiopaque reference markers, 23, 123, 223, 323, 423, and 523, centered on each of the six faces of the parallelpiped 33. The reference markers, 23, 123, 223, 323, 423, and 523, are marked with distinguishable indicia, such as X, Y, Z, $\hat{X}$, $\hat{Y}$, and $\hat{Z}$ so that the reference images cast by the markers, 23, 123, 223, 323, 423, and 523, can be identified easily and distinguished from one another. Alternatively or additionally, two or more of the edges of the parallelpiped 33 may be defined by radiopaque bars 26 such that the intersections of the bars 26 provide additional reference markers, such as reference marker 623 located at the intersection of the three bars labeled 26 in FIG. 14.

Figure 35:
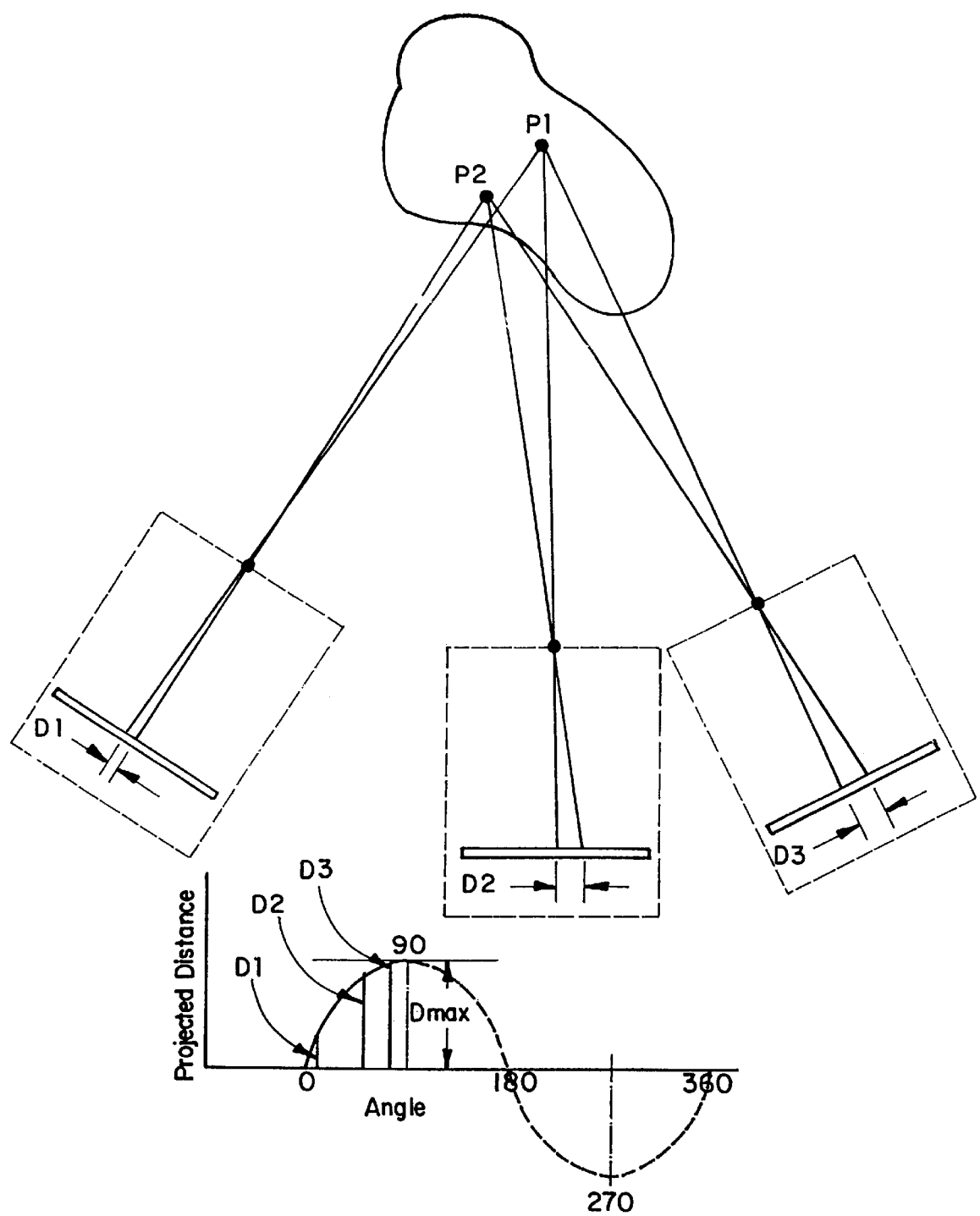
FIG. 35 is a schematic representation of a three-dimensional scaling calibration for determining the relative position of a camera in two planes orthogonal to the projection plane of the camera.

Alternatively, the six degrees of freedom for the radiation source 27 relative to the desired projection plane 37 (two translational, one displacement, two rotational, and one tilting degree of freedom) can be determined independently from the use of the fiducial reference when the orientation of the detector is fixed or known relative to either the object of interest or the radiation source. For example, the position of the radiation source 27 can be determined from multiple plane projections recorded from an arbitrarily positioned camera provided that the lens aperture is adjusted such that the entire object always appears in focus. The three relative angles associated with each projection are determined by attaching three orthogonally oriented angle sensing devices, such as gyroscopes, to the camera. The displacement of the radiation source relative to the object is determined using a range finder associated with the camera. Since the position of the camera within a plane parallel to the camera's projection plane is used only to determine the three-dimensional geometric relationships underlying the disparity observed between object images, the remaining degrees of freedom need only be measured relative to one another and, therefore, can be fixed from a geometric analysis of paired point projections. Referring to FIG. 35, it can be seen that, when the arbitrary camera positions are compensated for displacement and projection orthogonality, the projected distances, D1, D2, and D3, between the paired points P1 and P2 are a sinusoidal function of the corrected projection angle. Hence, the actual distance between P1 and P2 can be estimated from a non-linear curve fit to the observed projection distances.

Figure 34:
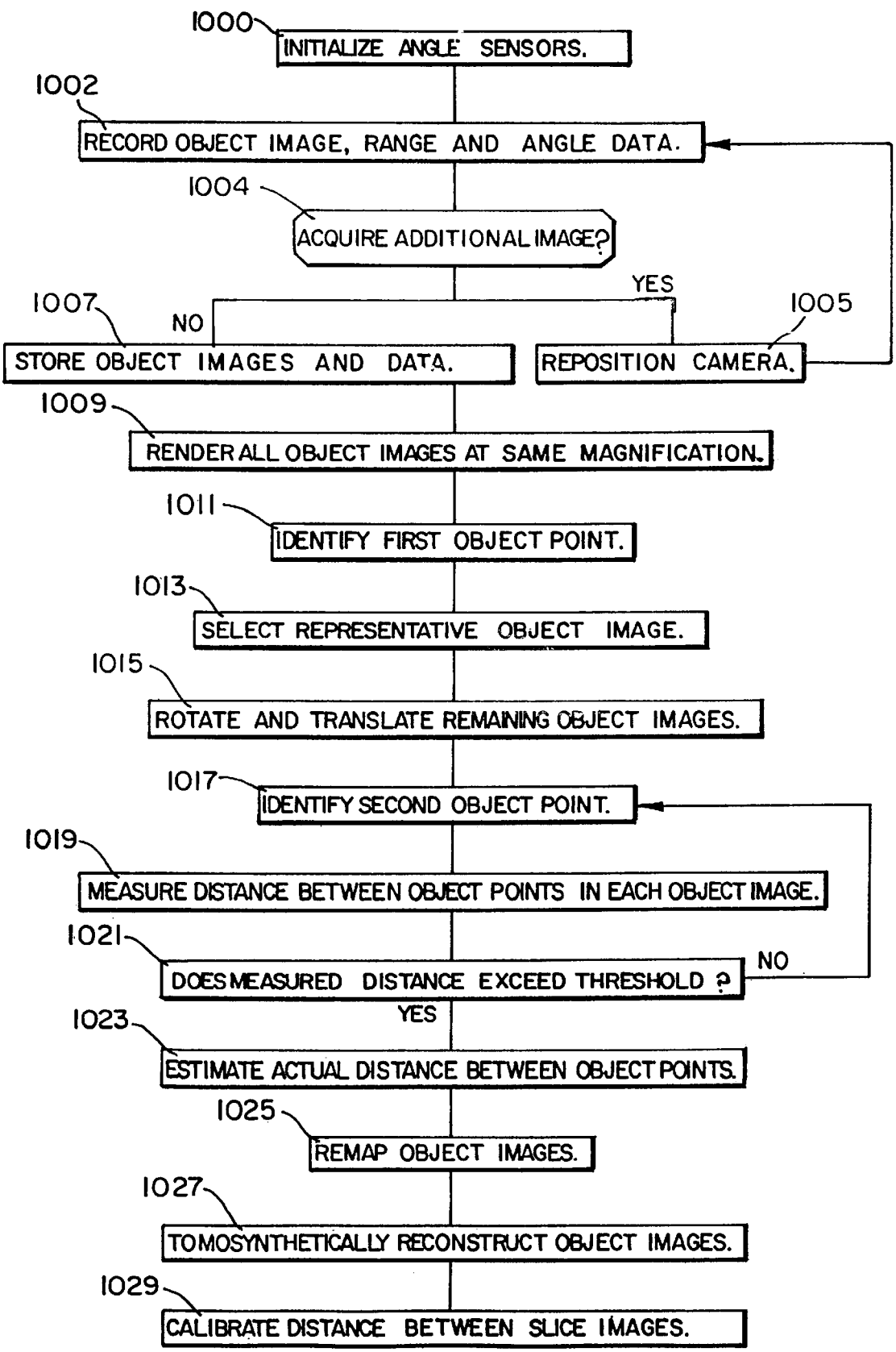
FIG. 34 is a flow chart showing the steps of a method for producing a three-dimensional representation of a stationary object from multiple plane projections recorded by an arbitrarily positionable camera.

A method for determining the position of the radiation source relative to the object using an arbitrarily positionable camera in accordance with the present invention is depicted in FIG. 34. At step 1000, angle sensors attached to the camera are initialized in order to eliminate possible drift in accuracy. The object is then roughly centered within the viewfinder of the camera and an object image, the nominal displacement of the camera from the object, and the angle data are recorded at step 1002. An intrinsic range finder associated with the camera is used to determine the nominal distance from the camera to the object of interest and the angle sensors are used to determine the angle data.

At step 1004, it is determined whether additional object images are desired. If additional object images are desired, the camera is repositioned at step 1005 and the process returns to step 1002. It should be appreciated that a minimum of three object images is required to produce a meaningful sinusoidal regression, as discussed in detail below. If no additional object images are to be recorded, the recorded object images and data is optionally stored in a computer readable format and the process proceeds to step 1007.

Each of the object images is then individually scaled to render all of the object images at the same magnification at step 1009. The scaling is possible using the range recorded for each object image because the linear magnification is inversely proportional to the range. By scaling the object images, an effective displacement between the camera and the object can be defined.

At step 1011, a first object point, visible on all of the projected object images, is selected. A representative object image is then selected at step 1013. The representative object image should be the object image which best approximates the orientation to which desired reconstructed tomosynthetic slices are to be parallel.

Each object image is then rotated and translated, at step 1015, so that all of the object images are brought into tomosynthetic registration. Specifically, each object image is rotated by an amount sufficient to adjust the rotational orientation of the camera about an axis perpendicular to the projection plane to match that of the representative object image. Rotational adjustment of the object images assures that the registrations which follow will not exclude a second reference point, whose selection is discussed below. Each rotated object image is then translated both vertically and horizontally by an amount which causes superposition of the projected image of the first object point within each object image with the projected image of the first object point within the representative object image.

At step 1017, a second object point visible on all of the scaled, rotated, and translated object images is selected. The distance between the projected images of the second object point and the first object point is measured, at step 1019, for each of the object images. If the relative change in distance does not exceed a task-dependent threshold value and produce a well-distributed range of values, the accuracy of the subsequent non-linear regression may be compromised. Accordingly, at step 1021, it is determined whether the measured distances exceed the task-dependent threshold. If the threshold is not exceeded, a new second object point is selected at step 1017. If the threshold is exceeded, the process proceeds to step 1023.

At step 1023, the actual distance between the first object point and the second object point is estimated from the measured distance separating the projected images of the first and second object points in the recorded object images. The estimate of the actual distance is determined using the effective displacement of the camera from the object and a sinusoidal curve fitting procedure, as well as the projection angle defined by a line connecting the first and second object points and the plane of the representative object image.

Using affine projection geometry, the recorded angle data, and the recorded displacement data, each object image is remapped onto the plane defined by the representative object image selected above at step 1025. The remapping is performed using the first object point as the common point of superposition. At step 1027, the object images are then tomosynthetically reconstructed using the second object point as a disparity marker. The distances between object images is then calibrated, at step 1029, using the estimate for the distance between the first and second object points and trigonometrically correcting the object images for foreshortening caused by variations in the projection angle.

Figure 36:
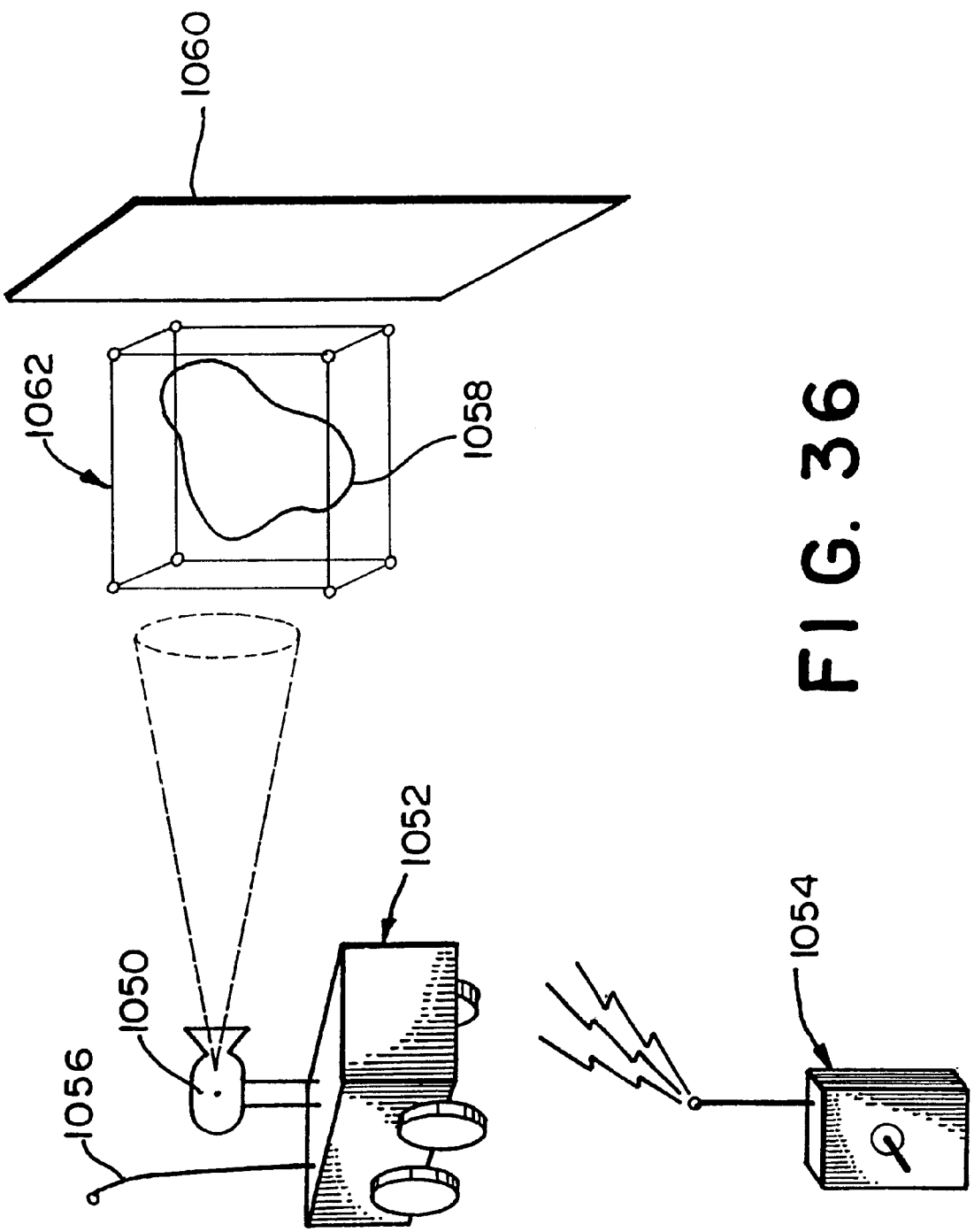
FIG. 36 is a schematic representation of a remote-controlled mobile radiation source.

Referring to FIG. 36, one arrangement for unconstraining and uncoupling the radiation source from the selected object is depicted. As shown in the figure, a radiation source 1050 is mounted on a mobile carriage 1052. The carriage 1052 is controlled remotely using a transmitter 1054 which transmits a signal to the carriage 1052 through an antenna 1056. In operation, the transmitter 1054 is operated to maneuver the carriage 1052, and thereby the radiation source, 1050, to move around a selected object 1058 to enable projected images of the object 1058 to be recorded on a detector 1060 at a variety of relative positions of the radiation source 1050, the object 1058 and fiducial reference 1062, and the detector 1060. In order to provide essentially complete freedom in positioning the radiation source 1050 relative to the object 1058 and fiducial reference 1062, the elevation and angle of tilt of the radiation source 1050 relative to the object 1058 and fiducial reference 1062 is also controllable through the transmitter 1054.

Reducing the uncertainty of the projection geometry through the constraint of one or more degrees of freedom reduces the complexity of the resulting reconstruction. An arrangement of the system of the present invention which is somewhat constrained is depicted in FIGS. 12 and 13, wherein a hand-held X-ray source is provided such that the orthogonal distance between the radiation source 127 and the recording medium 131 is fixed by a C-arm 129 at a distance short enough so that the image cast by the fiducial reference 122 is magnified relative to the size of the actual fiducial reference 122. Preferably, the C-arm 129 is connected to the recording medium 131 by a concentric swivel collar 149 to allow the C-arm 129 to be rotated relative to the recording medium 131. A disposable and crushable radiolucent foam cushion 130 may be attached to the surface of the recording medium 131 to permit comfortable customized stable adaptation of the detector 131 to the object 121. The other end of the C-arm 129 is attached to a potted X-ray source 145 so that radiation emanating from the potted X-ray source 145 impinges upon the recording medium 131. A trigger 146 is provided for operating the source 127. The source 127 optionally comprises a circular beam collimator 147 for collimating radiation emanating from the source 127. The collimator 147 may provide a relatively long focal-object distance to provide nearly affine projection geometries. Preferably, a handle 148 is also provided to enable the operator to more easily maneuver the source 127. The hand-held X-ray source 127 is connected to a computer/high voltage source 128 for controlling operation of the device. In addition, a disposable plastic bag 132 can be positioned around the detector 131 for microbial isolation. The source 127 can optionally comprise a rotatable transparent radiopaque plastic cylinder 119 and a transparent radiopaque shield 152 to protect the operator from scattered radiation. In this arrangement, there are 3 degrees of freedom (two translational and one displacement for the radiation source 127). Accordingly, a fiducial reference compensating for at least three degrees of freedom is necessary to completely describe or analyze the system. One convenient embodiment for solving the system depicted in FIGS. 12 and 13 employs a fiducial reference 122 comprising a single radiopaque sphere of finite diameter. Under those conditions, the length of the minor axis of the resulting elliptical shadow plus two translational measurements are sufficient to define the projection geometry completely.

Figure 17:
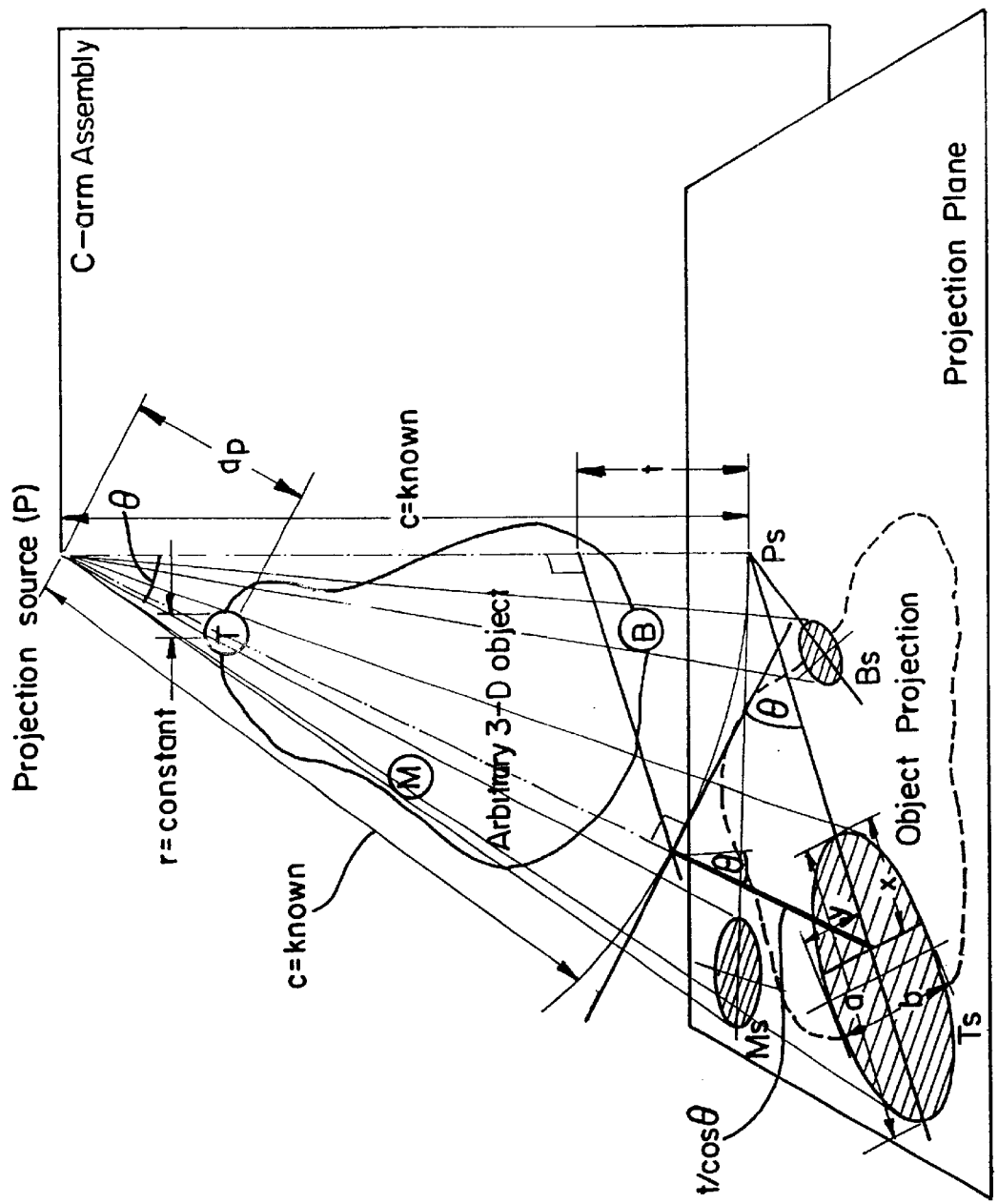
FIG. 17 is a schematic representation of the parameters associated with a system comprising three spherical, non-collinear reference markers wherein the orthogonal distance between the radiation source and the recording medium is fixed at a distance short enough so that the images cast by the reference markers are magnified relative to the size of the actual reference markers.
Figure 18:
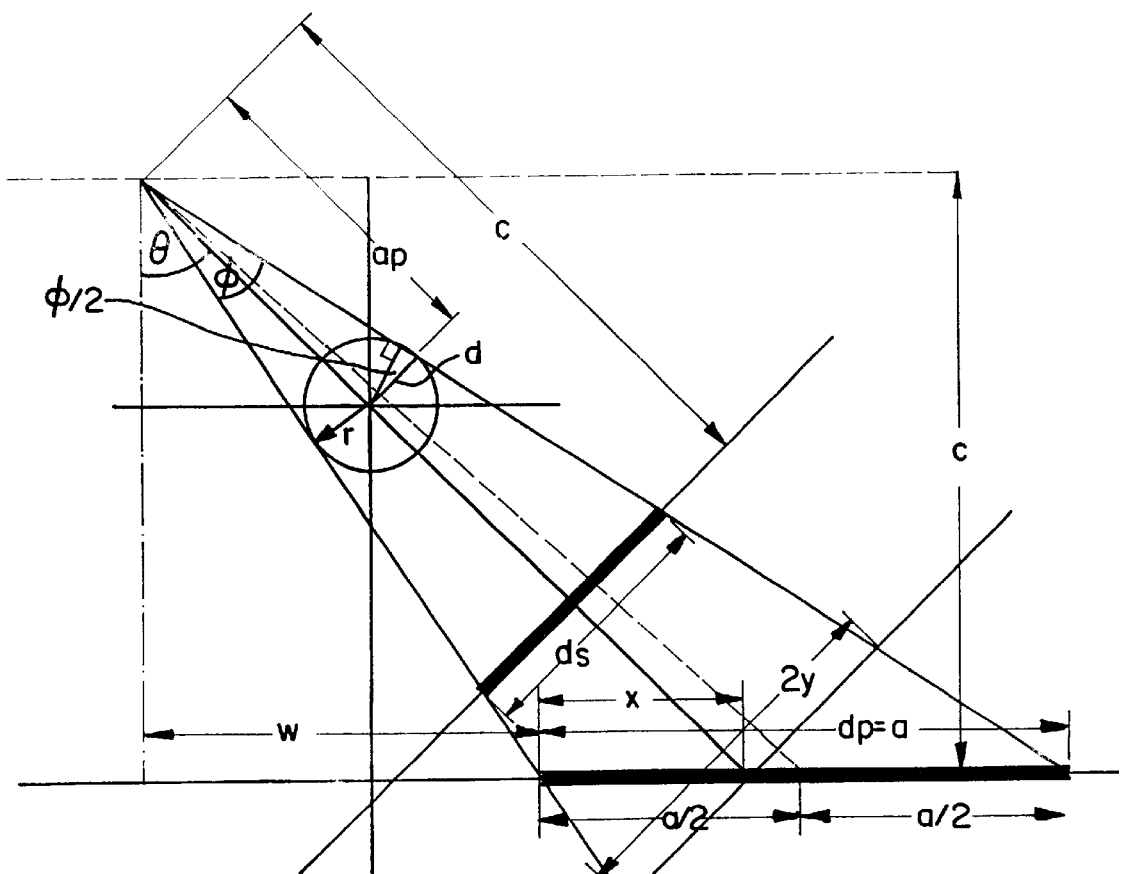
FIG. 18 is a schematic representation of the relevant parameters associated with a reference image associated with a spherical reference marker.
Figure 19:
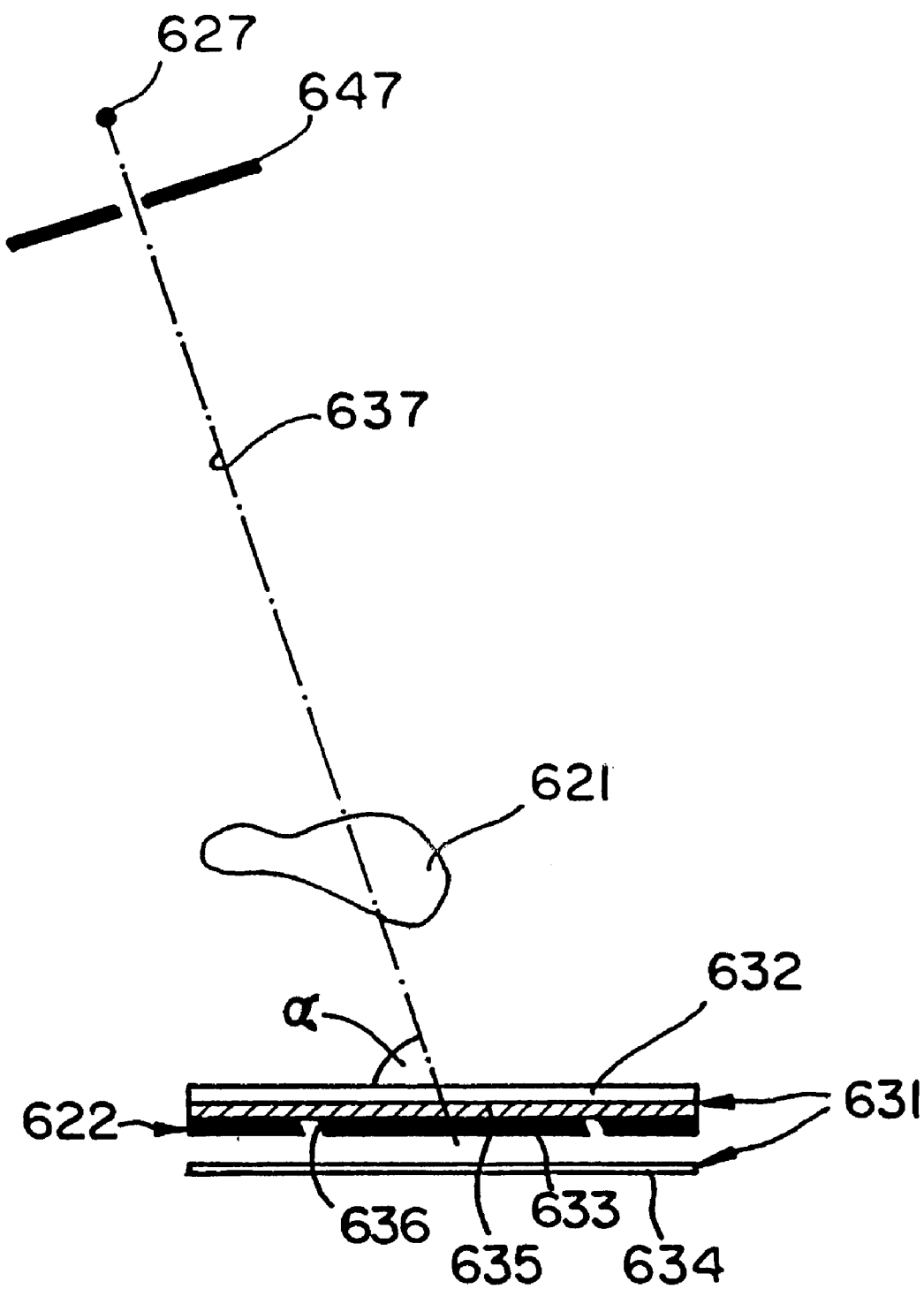
FIG. 19 is a schematic representation of an embodiment of the present invention wherein the fiducial reference comprises a radiopaque shield with a ring-like aperture.

The computational steps involved in synthesizing a three-dimensional image using three spherical, non-linear reference markers in a system wherein the orthogonal distance between the radiation source and the recording medium is fixed at a distance short enough so that the images cast by the reference markers are magnified relative to the size of the actual reference markers (i.e., a system with eight degrees of freedom as depicted in FIGS. 12 and 13) can be derived with reference to FIGS. 17 and 19. In the drawings, c is the fixed distance between the source and the projection plane; $P_s$ is the orthogonal projection of the source onto the projection plane; B, M, and T are the reference markers; r is the radius of the reference markers; $a_p$ is the distance from the center of a reference marker to the source; $\theta$ is the angle subtended by the center of a reference marker relative to a line orthogonal to the projection plane through the source; $\Phi$ is the angle at the apex of an isosceles triangle having a base of length r and a height of length $a_p$; $B_s$, $M_s$, and $T_s$ are the reference images associated with the reference markers; a (or, alternatively, $d_p$) is the major diameter of the reference images; b is the minor diameter of the reference images; x is the length of a section of an arc associated with a reference image measured from the projection of the center of the corresponding reference marker onto the projection plane along the major diameter, b, in a direction toward $P_s$; y is the length of an arc associated with a reference image through the projection of the center of the corresponding reference marker onto the projection plane and parallel to the minor diameter of the reference image; and $d_s$ is the major diameter of a reference image in a virtual projection plane.

Figure 6:
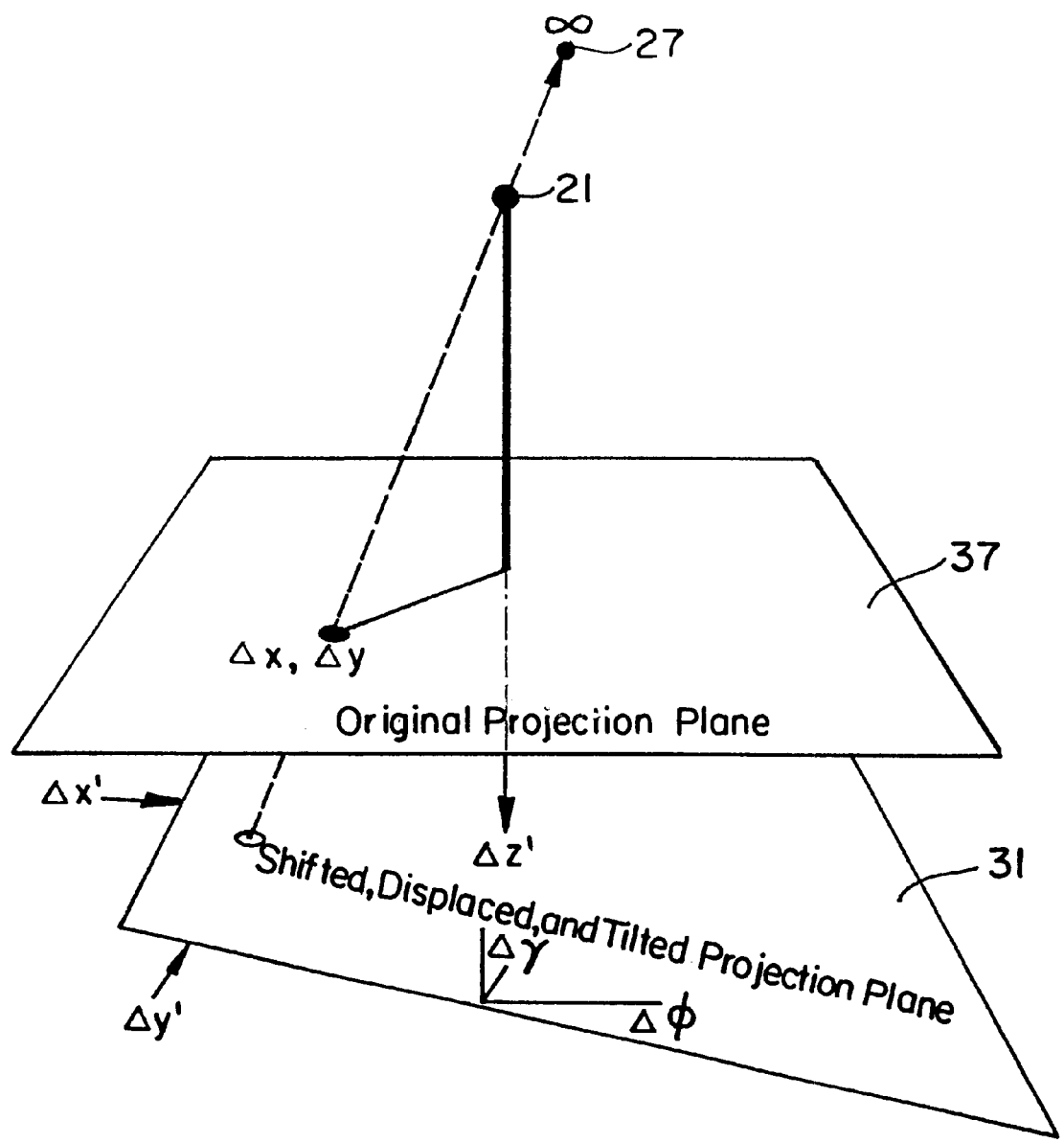
FIG. 6 is a schematic representation of a system having seven degrees of freedom in which an infinite point source is shifted relative to an original projection plane and in which a projection plane of a recording medium is shifted, displaced, and tilted relative to the original projection plane.

In FIG. 6, another arrangement of the system of the present invention is depicted wherein the radiation source 27 is located at a fixed distance from the selected object 21 and sufficiently far so that magnification is not significant. However, the recording medium 31 is allowed to be shifted, displaced, and tilted relative to the selected object 21 and an original or desired projection plane 37. In this arrangement, there are seven degrees of freedom (two translational degrees of freedom for the radiation source 27 and 2 translational, 1 displacement, and 2 tilting degrees of freedom for the recording medium 31). Therefore, a fiducial reference having at least seven degrees of freedom is needed to solve the system. Accordingly, a fiducial reference comprising at least four point-size reference markers can be used to determine the position of the radiation source relative to the selected object 21 and the recording medium 31.

Figure 7:
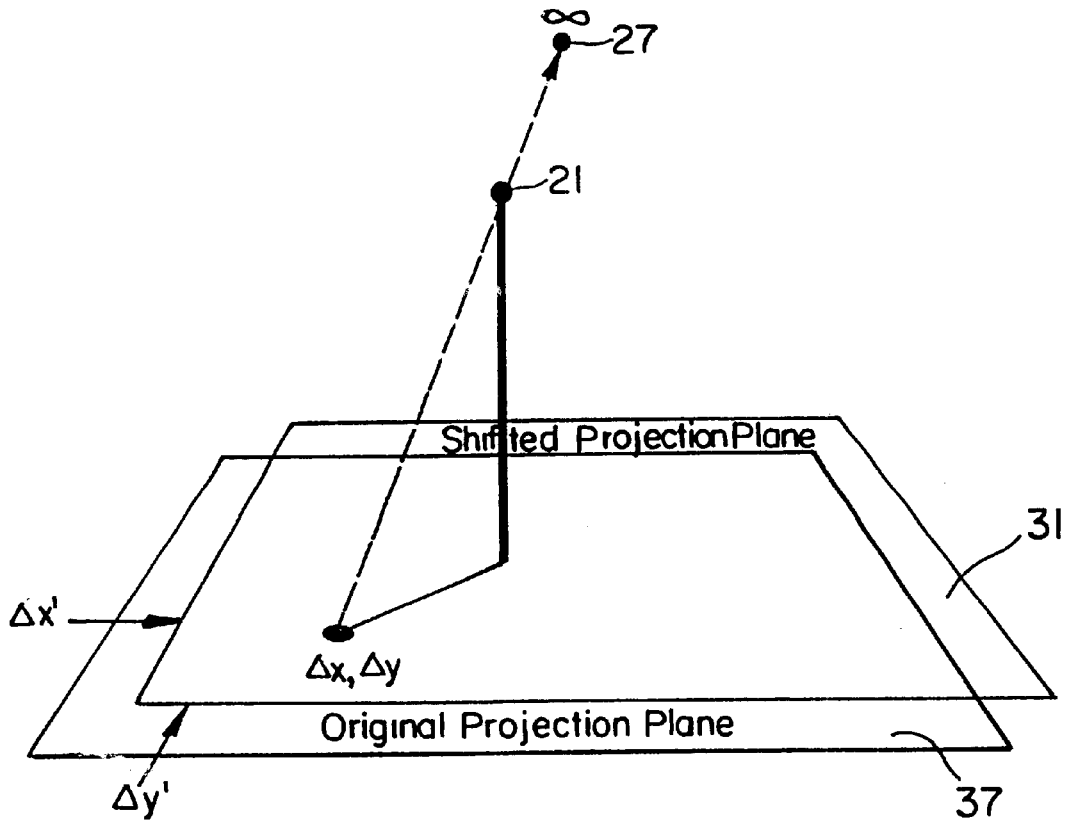
FIG. 7 is a schematic representation of a system having four degrees of freedom in which an infinite point source is shifted relative to an original projection plane and in which a projection plane of a recording medium is shifted relative to the original projection plane.

In FIG. 7, yet another arrangement of the system of the present invention is depicted wherein the distance between the object 21 and the radiation source 27 is sufficiently large so that magnification can be ignored and wherein the recording medium 31 is free to shift laterally relative to the object 21 and the desired or original projection plane 37. In this arrangement, there are four degrees of freedom (two translational degrees of freedom for the radiation source 27 and two translational degrees of freedom for the recording medium 31). Therefore, a fiducial reference having at least four degrees of freedom is necessary to completely determine the system. Accordingly, a fiducial reference comprising at least two point-size reference markers can be used to determine the position of the radiation source relative to the selected object 21 and the recording medium 31. This relatively constrained system may be useful in three-dimensional reconstructions of transmission electron micrographs produced from video projections subtending various degrees of specimen tilt and exhibiting various amounts of arbitrary and unpredictable lateral shift due to intrinsic instability associated with the instrument's electron lenses.

Referring to FIG. 1, the radiation source 27 may be either a portable or a stationary X-ray source. However, the radiation source 27 is not limited to an X-ray source. The specific type of source 27 which is utilized will depend upon the particular application. For example, the present invention can also be practiced using magnetic resonance imaging (MRI), ultrasound, visible light, infrared light, ultraviolet light, or microwaves.

Figure 10:
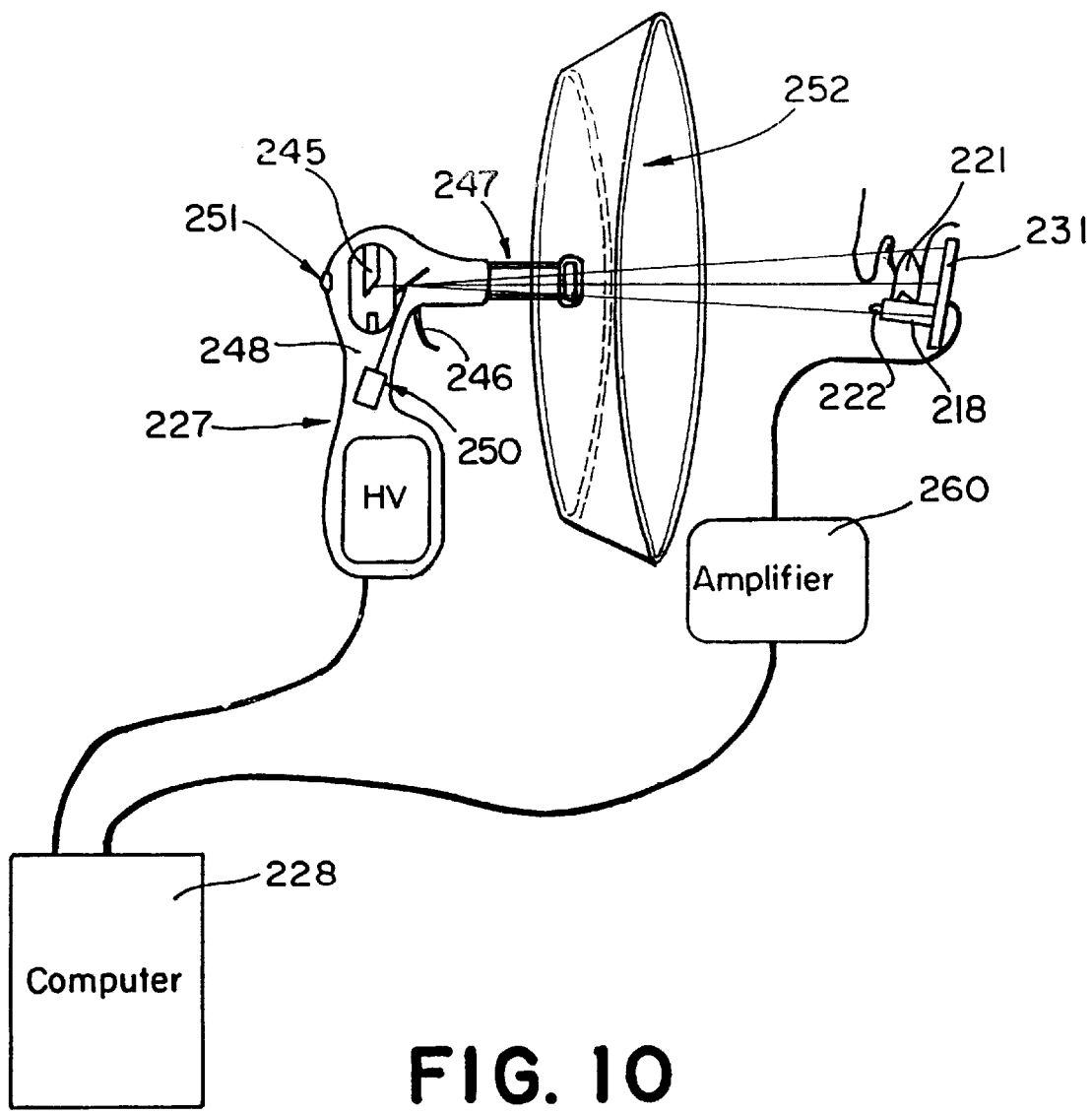
FIG. 10 is a schematic representation of an embodiment of the present invention wherein the source is a hand-held X-ray source with a laser aiming device.

In the embodiment shown in FIG. 10, the source 227 is a hand-held X-ray source, similar to that described above in reference to source 127, except that a low power laser aiming device 250 and an alignment indicator 251 are provided to insure that the source 227 and the recording medium 231 are properly aligned. In addition, a radiolucent bite block 218 is provided to constrain the detector 231 relative to the object 221, thereby constraining the system to three degrees of freedom (two translational and one displacement for the radiation source 227 relative to the object 221 and detector 231). Consequently, the fiducial reference 222 can be fixed directly to the bite block 218. When the source 227 is properly aligned with the recording medium 231, radiation emanating from the aiming device 250 impinges on the recording medium 231. In response to a measured amount of radiation impinging on the recording medium 231, a signal is sent to activate the alignment indicator 251 which preferably produces a visible and/or auditory signal. With the alignment indicator 251 activated, the X-ray source 245 can be operated at full power to record a projected image. In addition, the source 227 can optionally comprise a collimator 247 to collimate the radiation from the X-ray source and/or a transparent scatter shield 252 to protect the operator from scattered radiation. In lieu of the scatter shield 252, the operator can stand behind a radiopaque safety screen when exposing the patient to radiation from the source 227. A handle 248 and trigger 246 may be provided to facilitate the handling and operation of the source 227. The source 227 is connected to a computer/high voltage source 228 and an amplifier 260 for controlling operation of the device.

In one embodiment, the aiming device 250 comprises an X-ray source operated in an ultra-low exposure mode and the projected image is obtained using the same X-ray source operated in a full-exposure mode. Alternatively, a real-time ultra-low dose fluoroscopic video display can be mounted into the handle 248 of the source 227 via a microchannel plate (MCP) coupled to a CCD. The video display switches to a lower gain (high signal-to-noise) frame grabbing mode when the alignment is considered optimal and the trigger 246 is squeezed more tightly.

Figure 22:
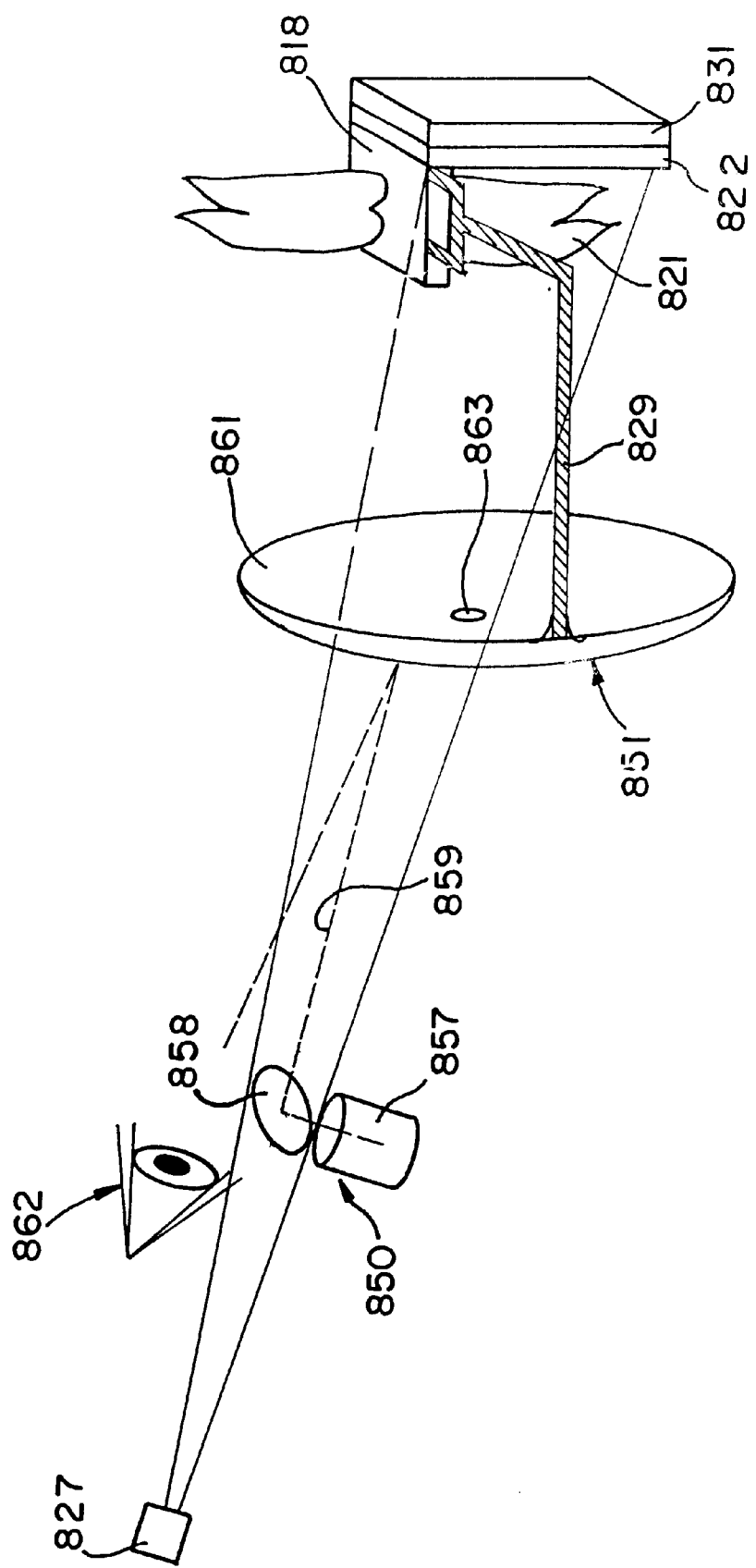
FIG. 22 is an alternate embodiment of a laser aiming device in accordance with the present invention.

An alternate embodiment of an aiming device in accordance with the present invention is shown in FIG. 22. The aiming device 850 comprises a laser source 857 and a radiolucent angled mirror 858 which produces a laser beam, illustrated by dashed line 859, which is concentric with the radiation emanating from the source 827. The alignment indicator 851 comprises a radiolucent spherical surface 861 which is rigidly positioned relative to the detector 831 by a C-arm 829 that is plugged into the bite block 818. When the aiming device 850 is aimed such that the laser beam 859 impinges upon the spherical surface 861, the specular component of the laser beam 859 is reflected by the spherical surface 861. Accordingly, proper alignment of the source 827, the object 821, and the detector 831 is obtained when the reflected portion of the laser beam 859 is within a small solid angle determined by the position of the aiming device 850. Direct observation of the reflected portion of the laser beam 859 by a detector or observer 862 can be used to verify the alignment. As shown in the figure, the fiducial reference 822 comprises a radiolucent spacer containing a fiducial pattern that is affixed to the detector 831. Further, a central ring area 863 can be designated at the center of the spherical surface 861 such that aiming the laser beam 859 at the central ring area 863 assures an essentially orthogonal arrangement of the source 827 and the detector 831. In addition, replacing the concentric laser source 857 with a laser source that produces two laser beams that are angled relative to the radiation emanating from the source 827 permits the distance between the source 827 and the detector 831 to be set to a desired distance, provided that the two laser beams are constrained to converge at the spherical surface 861 when the desired distance has been established.

Referring again to FIG. 1, the recording medium 31 is provided for recording the projected object image 40 of the selected object 21 and the projected reference images, 39 and 139, of the reference markers 23 and 123. The recording medium 31 may be in the form of a photographic plate or a radiation-sensitive, solid-state image detector such as a radiolucent charge-coupled device (CCD).

Figure 8:
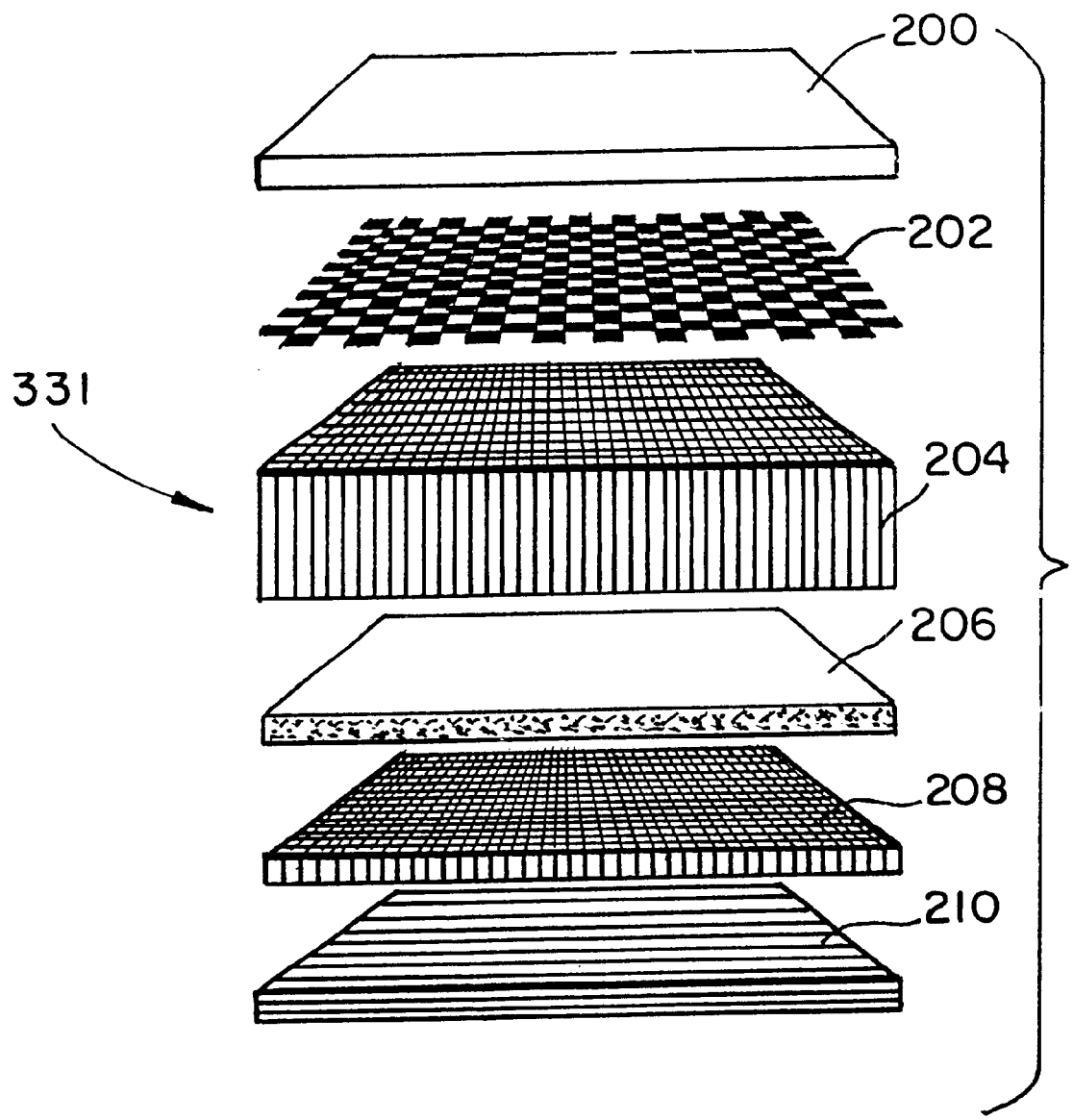
FIG. 8 is an exploded, schematic representation of a charge-coupled device (CCD) for use as a recording medium with intrinsic components enabling automated determination of projective geometry.

In one particular embodiment depicted in FIG. 8, the recording medium 331 comprises a CCD having a top screen 200, a bottom screen 206 positioned below the top screen 200, and a detector 210 positioned below the bottom screen 206. The top screen 200 is monochromatic so that a projected image projected onto the top screen 200 causes the top screen 200 to fluoresce or phosphoresce a single color. In contrast, the bottom screen 206 is dichromatic, so that the bottom screen 206 fluoresces or phosphoresces in a first color in response to a projected image projected directly onto the bottom screen 206 and fluoresces or phosphoresces in a second color in response to fluorescence or phosphorescence from the top screen 200. The detector 210 is also dichromatic so as to allow for the detection and differentiation of the first and the second colors. The recording medium 331 may also comprise a radiolucent optical mask 202 to modulate the texture and contrast of the fluorescence or phosphorescence from the top screen 200, a radiolucent fiber-optic spacer 204 to establish a known projection disparity, and a radiopaque fiber-optic faceplate 208 to protect the detector 210 from radiation emanating directly from the radiation source.

Figure 20:
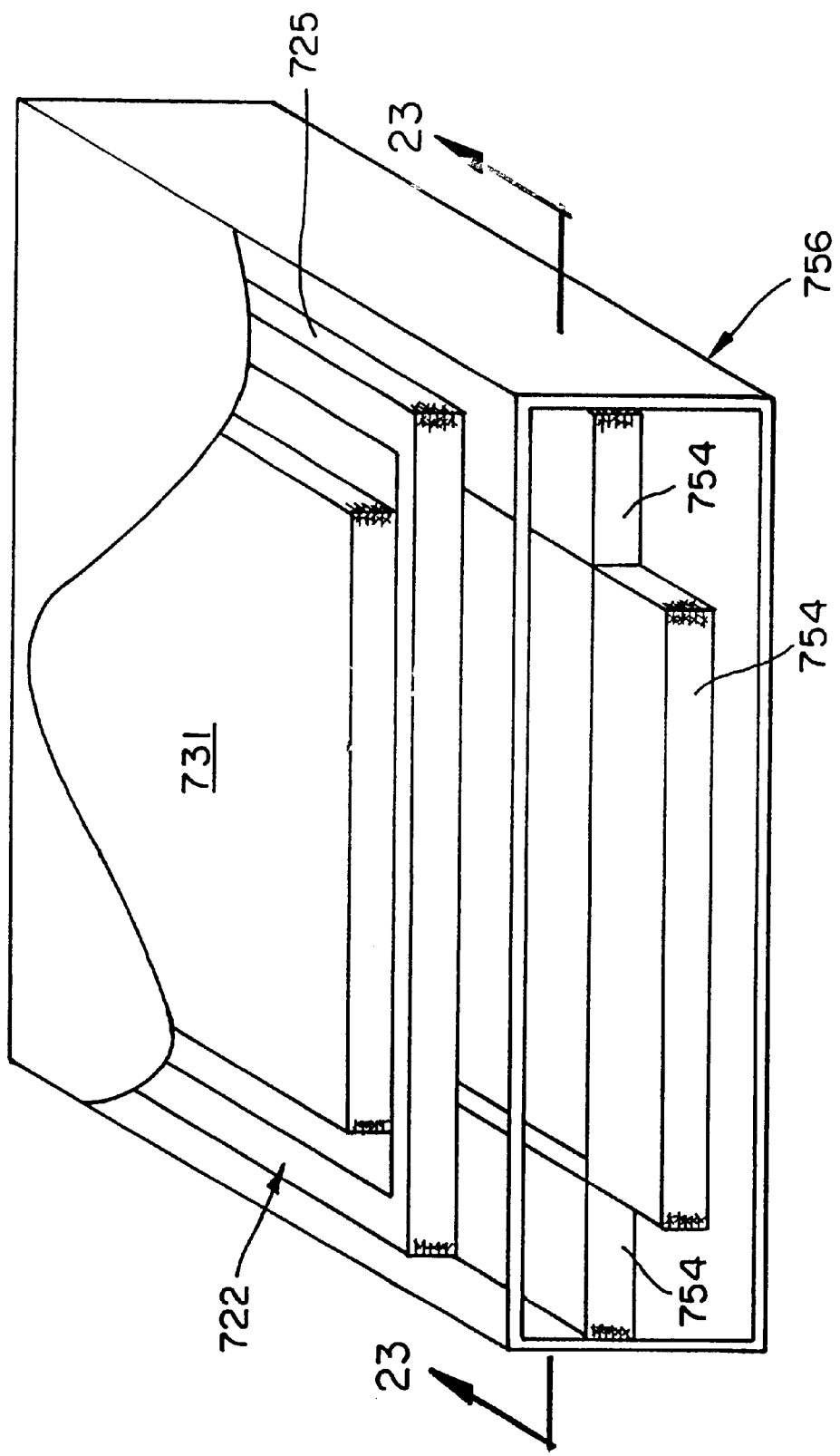
FIG. 20 is a schematic, perspective view of an embodiment of the present invention, wherein the detector comprises a charge-coupled device (CCD) and the fiducial reference comprises a frame, shown with the front and a section of the top removed.
Figure 21:
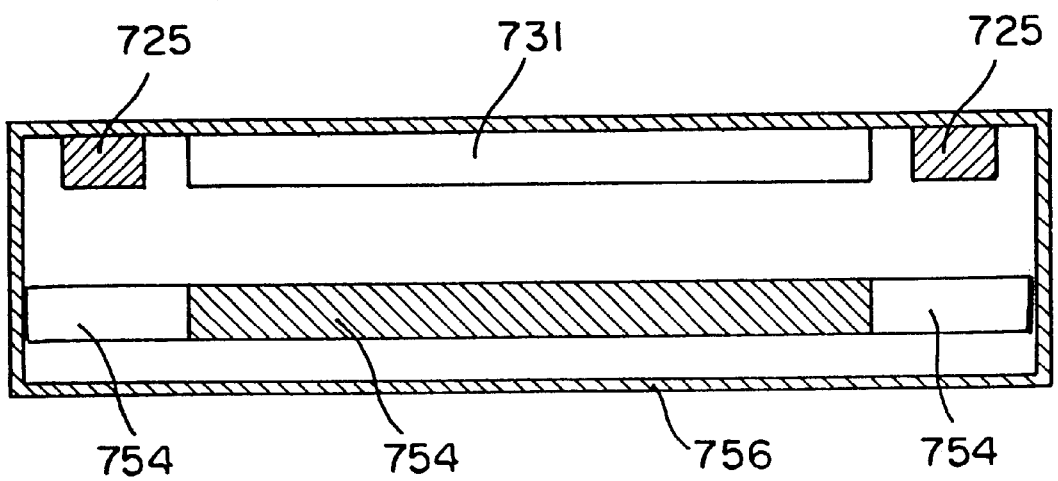
FIG. 21 is a sectional view of the embodiment depicted in FIG. 20 taken along the 23—23 line.

Yet another embodiment is depicted in FIGS. 20 and 21, wherein the detector 731 comprises a phosphor-coated CCD and the fiducial reference 722 comprises a radiopaque rectangular frame 725. Both the detector 731 and the fiducial reference 722 are contained within a light-tight package 756. The detector 731 and fiducial reference 722 are preferably positioned flush with an upper, inner surface of the package 756. The dimensions of the frame 725 are selected such that the frame 725 extends beyond the perimeter of the detector 731. Phosphor-coated strip CCDs 754 are also contained within the package 756. The strip CCDs 754 are positioned below the frame 725 such that radiation impinging upon the frame 725 castes an image of each edge of the frame 725 onto one of the strip CCDs 754. The positions of the frame shadow on the strip CCDs 754 is used to determine the projection geometry.

Figure 9:
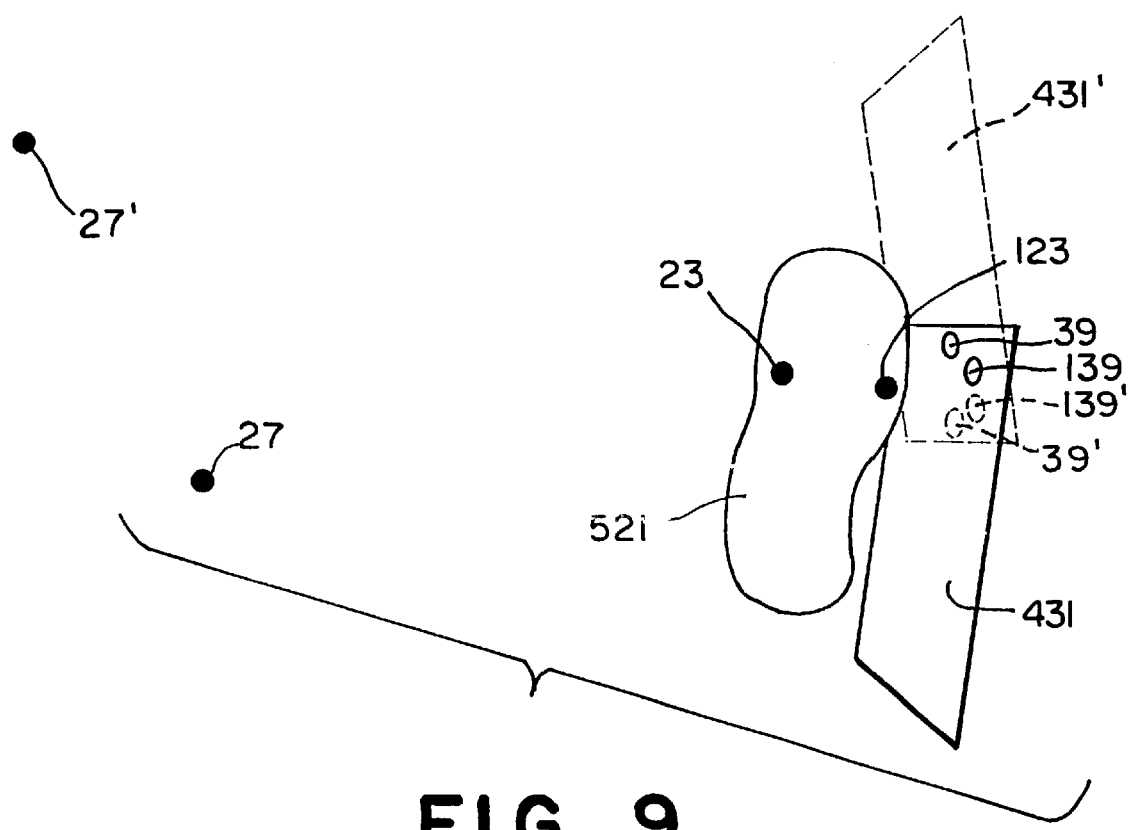
FIG. 9 is a schematic representation of an embodiment of the present invention wherein the recording medium is smaller than the projected image of the object.

In the embodiment shown in FIG. 9, the recording medium 431 is smaller than the projected image of object 521. Provided that the reference images, 39 and 139, corresponding to the reference markers, 23 and 123, can be identified on all the projected images, image slices extending across the union of all the projected images can be obtained. This is illustrated schematically in FIG. 9, wherein the reference images, 39 and 139, are taken with the source 27 and the recording medium 431 in the image positions indicated by the solid lines. Similarly, the dashed images, 39' and 139', are taken with the source 27' and the recording medium 431' in the positions indicated by the dashed lines. Accordingly, image slices of an object which casts an object image that is larger than the recording medium 431 can be synthesized. Further, by using multiple fiducial references spaced in a known pattern which are all linked to the object of interest, additional regions of commonality can be identified between multiple overlapping projection geometries, so that a region of any size can be propagated into a single, unified reconstruction. Thus, it is possible to accommodate an object much larger than the recording medium used to record individual projection images.

Figure 37:
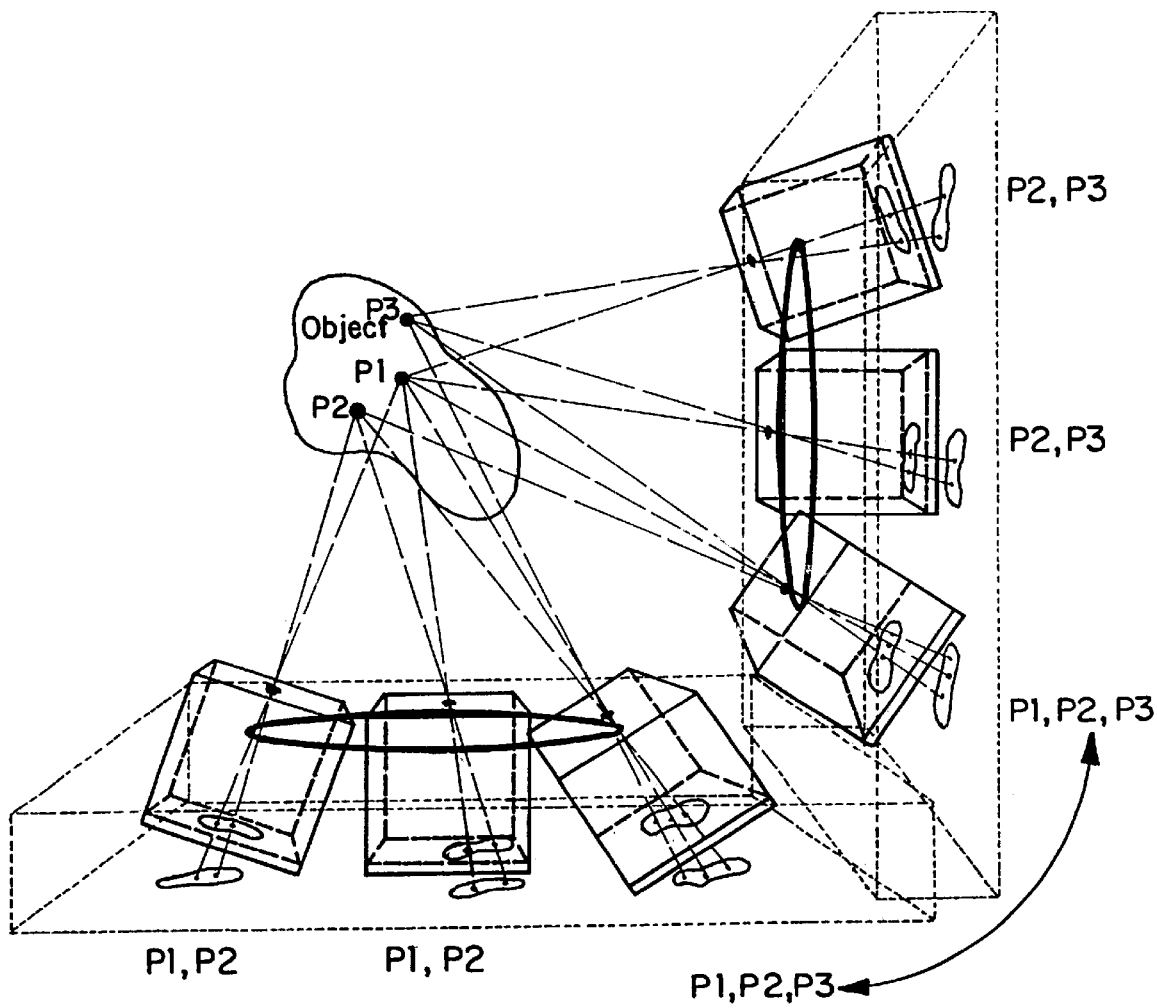
FIG. 37 is a schematic representation of an embodiment of the present invention wherein a camera is used to record overlapping sets of projected images.

Similarly, as depicted in FIG. 37, regions of overlap between two or more sets of projected images recorded can be used as a basis for extrapolating registration and calibration of the sets of projected images. As shown, a first set of projected images is recorded using an X-ray camera configured to provide a first aperture. A second set of projected images is then recorded using the camera configured to provide a second aperture. The first and second sets of projected images are then brought into alignment by identifying fiducial reference points that are common to the overlapping regions of the projected images.

Figure 2:
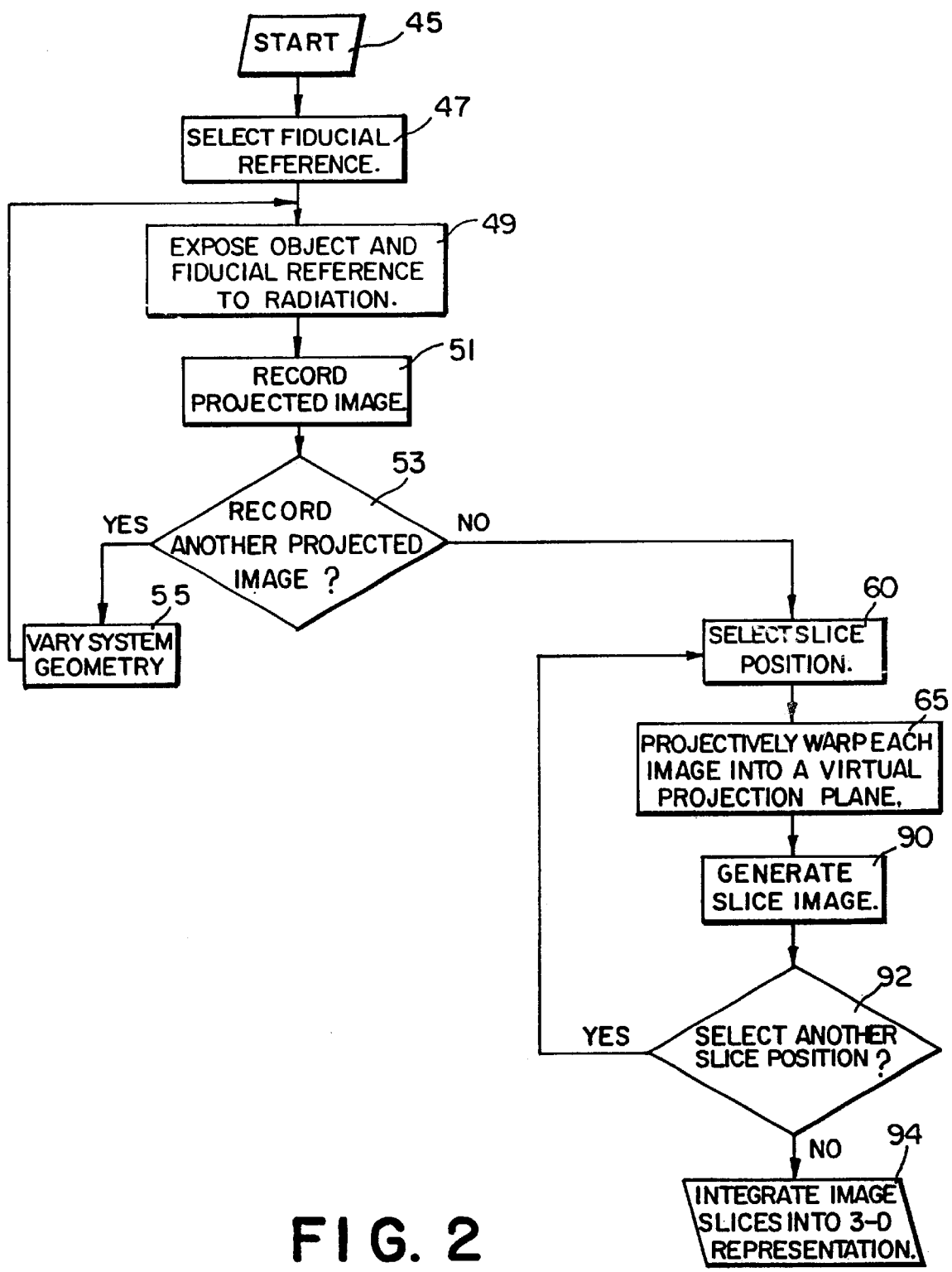
FIG. 2 is a flow chart showing the steps involved in creating three-dimensional radiographic displays using computed tomography in accordance with the present invention.

The present invention also relates to a method for creating a slice image through the object 21 of FIG. 1 from a series of two-dimensional projected images of the object 21, as shown in FIG. 2. The method of synthesizing the image slice starts at step 45. Each step of the method can be performed as part of a computer-executed process.

At step 47, a fiducial reference 22 comprising at least two reference markers, 23 and 123, is selected which bears a fixed relationship to the selected object 21. Accordingly, the fiducial reference 22 may be affixed directly to the selected object 21. The minimum required number of reference markers 23 is determined by the number of degrees of freedom in the system, as discussed above. When the fiducial reference 22 comprises reference markers 23 of a finite size, the size and shape of the reference markers 23 are typically recorded.

The selected object 21 and fiducial reference 22 are exposed to radiation from any desired projection geometry at step 49 and a two-dimensional projected image 38 is recorded at step 51. Referring to FIG. 1, the projected image 38 contains an object image 40 of the selected object 21 and a reference image, 39 and 139, respectively, for each of the reference markers 23 and 123 of the fiducial reference 22.

At step 53, it is determined whether additional projected images 38 are desired. The desired number of projected images 38 is determined by the task to be accomplished. Fewer images reduce the signal-to-noise ratio of the reconstructions and increase the intensities of component "blur" artifacts. Additional images provide information which supplements the information contained in the prior images, thereby improving the accuracy of the three-dimensional radiographic display. If additional projected images 38 are not desired, then the process continues at step 60.

If additional projected images 38 are desired, the system geometry is altered at step 55 by varying the relative positions of (1) the radiation source 27, (2) the selected object 21 and the fiducial reference 22, and (3) the recording medium 31. The geometry of the system can be varied by moving the radiation source 27 and/or the recording medium 31. Alternatively, the source 27 and recording medium 31, the selected object 21 and fiducial reference 22 are moved. When the radiation source and recording medium produce images using visible light (e.g., video camera), the geometry of the system must be varied to produce images from various sides of the object in order to obtain information about the entire object. After the system geometry has been varied, the process returns to step 49.

After all of the desired projected images have been recorded, a slice position is selected at step 60. The slice position corresponds to the position at which the image slice is to be generated through the object.

Figure 3:
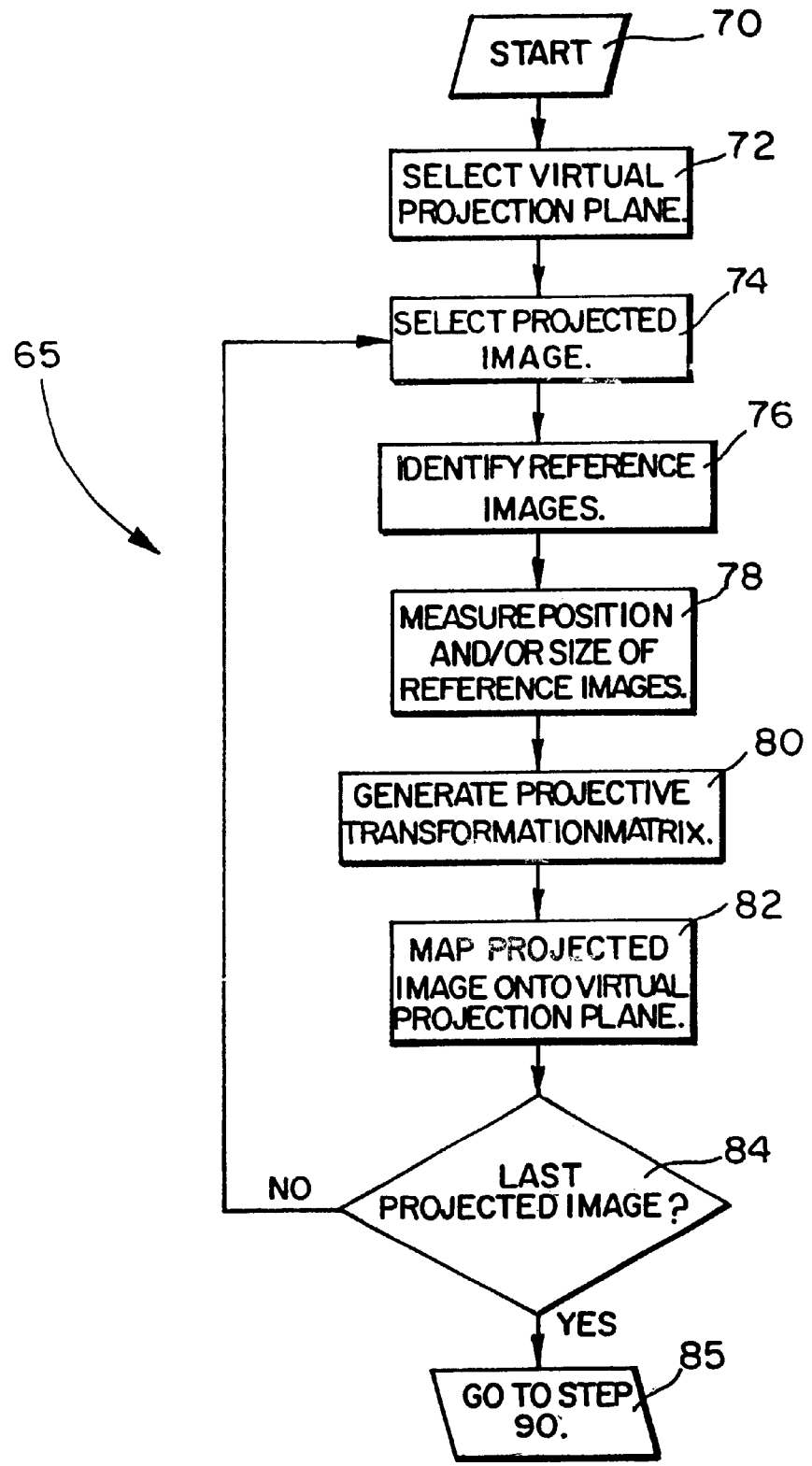
FIG. 3 is a flow chart showing details of a method of projectively warping or transforming a projected image from an actual plane of projection onto a virtual projection plane.

After the slice position has been selected, each projected image 38 is projectively warped onto a virtual projection plane 37 at step 65. The warping procedure produces a virtual image corresponding to each of the actual projected images. Each virtual image is identical to the image which would have been produced had the projection plane if been positioned at the virtual projection plane with the projection geometry for the radiation source 27, the selected object 21, and the fiducial reference 22 of the corresponding actual projected image. The details of the steps involved in warping the projection plane 37 are shown in FIG. 3. The process starts at step 70.

At step 72, a virtual projection plane 37 is selected. In most cases it is possible to arrange for one of the projected images to closely approximate the virtual projection plane position. That image can then be used as the basis for transformation of all the other images 38. Alternatively, as shown for example in FIG. 4, if the fiducial reference 22 comprises more than two co-planar reference markers 23, a plane which is parallel to the plane containing the co-planar reference markers 23 can be selected as the virtual projection plane 37. When the virtual projection plane 37 is not parallel to the plane containing the co-planar reference markers 23, although the validity of the slice reconstruction is maintained, the reconstruction yields a slice image which may be deformed due to variations in magnification. The deformation becomes more prominent when the magnification varies significantly over the range in which the reconstruction is carried out. In such cases, an additional geometric transformation to correct for differential magnification may be individually performed on each projected image 38 to correct for image deformation.

One of the recorded projected images 38 is selected at step 74 and the identity of the reference images 39 cast by each reference marker 23 is determined at step 76. In the specialized case, such as the one shown in FIG. 1, where spherical reference markers 23 of the same radius are used and the relative proximal distance of each reference marker 23 to the radiation source 27 at the time that the image 38 was recorded is known, assignment of each elliptical image 39 to a corresponding reference marker 23 can be accomplished simply by inspection. Under such conditions, the minor diameter of the elliptical image 39 is always larger the closer the reference marker 23 is to the radiation source 27. This is shown most clearly in FIG. 17 wherein the minor diameter of reference image B, corresponding to reference marker B is smaller than the minor diameter of reference image $T_s$ corresponding to reference marker T. Alternatively, when applied to radiation capable of penetrating the fiducial reference 22 (i.e., X-rays), spherical reference markers 23 which are hollow having different wall thicknesses and hence, different attenuations can be used. Accordingly, the reference image 39 cast by each spherical reference marker 23 can be easily identified by the pattern of the reference images 39. Analogously, spherical reference markers 23 of different colors could be used in a visible light mediated system.

Figure 16:
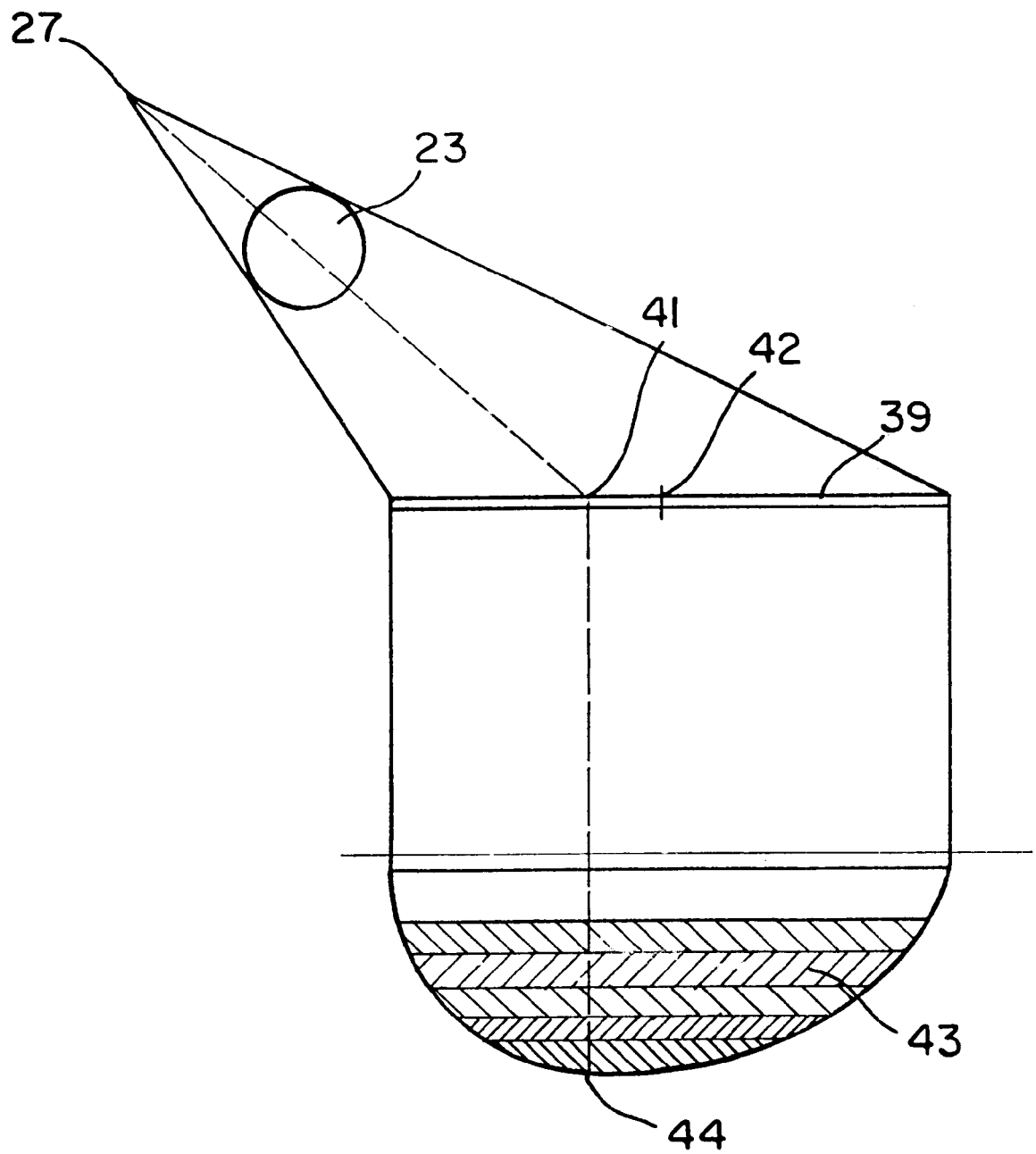
FIG. 16 is a schematic representation of a reference image cast by a spherical reference marker showing the resulting brightness profile.

The position of each reference image 39 cast by each reference marker 23 is measured at step 78. When a spherical reference marker 23 is irradiated by source 27, the projected center 41 of the reference marker 23 does not necessarily correspond to the center 42 of the reference image 39 cast by that reference marker 23. Accordingly, the projected center 41 of the reference marker 23 must be determined. One method of determining the projected center 41 of the reference marker 23 is shown in FIG. 16. The variation in intensity of the reference image 39 associated with reference marker 23 along the length of the major diameter of the reference image 39 is represented by the brightness profile 43. The method depicted in FIG. 16 relies on the fact that the projected center 41 always intersects the brightness profile 43 of the reference image 39 at, or very near, the maximum 44 of the brightness profile 43. Accordingly, the projected center 41 of a spherical reference marker 23 produced by penetrating radiation can be approximated by smoothing the reference image 39 to average out quantum mottle or other sources of brightness variations which are uncorrelated with the attenuation produced by the reference marker 23. An arbitrary point is then selected which lies within the reference image 39. A digital approximation to the projected center 41 is isolated by performing a neighborhood search of adjacent pixels and propagating the index position iteratively to the brightest (most attenuated) pixel in the group until a local maximum is obtained. The local maximum then represents the projected center 41 of the reference marker 23.

Returning to step 78 of FIG. 3, when the fiducial reference 22 comprises reference markers 23 of finite size, the sizes of each image 39 cast by each reference marker 23 are also recorded. For example, the lengths of the major and minor diameters of elliptical reference images cast by spherical reference markers 23 can be measured. Computerized fitting procedures can be used to assist in measuring the elliptical reference images 39 cast by spherical reference markers 23. Such procedures, which are well-known in the art, may be used to isolate the elliptical reference images 39 from the projected image 38 and determine the major and minor diameters of the reference images 39.

Because the attenuation of a spherical reference marker 23 to X-rays approaches zero at tangential extremes, the projected minor diameter of resulting elliptical reference images 39 will be slightly smaller than that determined geometrically by projection of the reference marker's actual diameter. The amount of the resulting error is a function of the energy of the X-ray beam and the spectral sensitivity of the recording medium 31. This error can be eliminated by computing an effective radiographic diameter of the reference marker 23 as determined by the X-ray beam energy and the recording medium sensitivity in lieu of the actual diameter.

One method of obtaining the effective radiographic diameter is to generate a series of tomosynthetic slices through the center of the reference marker 23 using a range of values for the reference marker diameter decreasing systematically from the actual value and noting when the gradient of the reference image 39 along the minor diameter is a maximum. The value for the reference marker diameter resulting in the maximum gradient is the desired effective radiographic diameter to be used for computing magnification.

Further, each projected image can be scaled by an appropriate magnification. For fiducial references 22 comprising spherical reference markers 23, the minor diameter of the reference image 39 is preferably used to determine the magnification since the minor diameter does not depend on the angle between the source 27 and the recording medium 31. Accordingly, the magnification of a spherical reference marker 23 can be determined from the measured radius of the reference marker 23, the minor diameter of the reference image 39 on the recording medium 31, the vertical distance between the center of the reference marker 23 and the recording medium 31, and the vertical distance between the recording medium 31 and the virtual projection plane 37.

Returning to FIG. 3 with reference to FIG. 1, a projection transformation matrix, representing a series of transformation operations necessary to map the selected projected image 38 onto the virtual projection plane 37, is generated at step 80. The projection transformation matrix is generated by solving each projected image 38 relative to the virtual projection plane 37. In one embodiment, the positions of the co-planar reference markers 23 are used to determine the transformation matrix by mapping the position of the reference images 39 cast by each co-planar reference marker 23 in the projected image onto its corresponding position in the virtual projection plane. For example, when the fiducial reference comprises a radiopaque frame 25, the positions of the reference images 39 cast by the reference markers 23 formed at the corners of the frame 25 are mapped to a canonical rectangle having the same dimensions and scale as the frame 25. This approach also serves to normalize the projective data. Depending on the number of degrees of freedom, the transformation operations range from complex three-dimensional transformations to simple planar rotations or translations. Once the projective transformation matrix has been generated, the matrix is used to map the projected image 38 onto the virtual projection plane 37 at step 82.

At step 84, it is determined whether all of the projected images 38 have been analyzed. If all of the projected images 38 have not been analyzed, the process returns to step 74, wherein an unanalyzed image 38 is selected. If no additional projected images 38 are to be analyzed, then the process proceeds through step 85 of FIG. 3 to step 90 of FIG. 2.

After each image has been warped onto the virtual projection plane, an image slice through the object 21 at the selected slice position is generated at step 90. An algorithm, such as that described in U.S. Pat. No. 5,359,637, which is incorporated herein by reference, can be used for that purpose. The position of the reference image cast by the alignment marker or markers 23 in each projected image 38 are used as the basis for application of the algorithm to generate the image slices.

By generating image slices at more than one slice position, a true three-dimensional representation can be synthesized. Accordingly, it is determined whether an additional slice position is to be selected at step 92. If an additional slice position is not desired, the process proceeds to step 94. If a new slice position is to be selected, the process returns to step 60.

Figure 28:
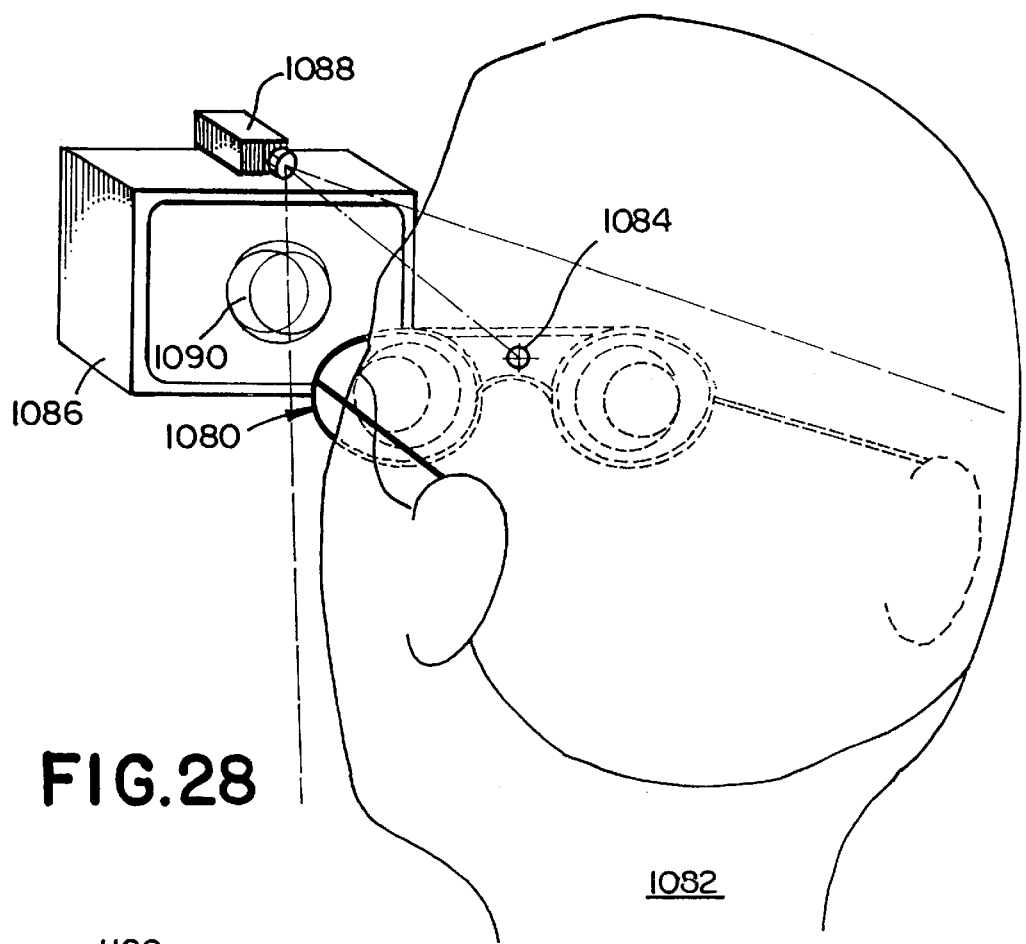
FIG. 28 is a schematic representation of a pseudo-holographic image display.

If image slices at multiple slice positions have been generated, the entire set of image slices is integrated into a single three-dimensional representation at step 94. Alternative bases for interactively analyzing and displaying the three-dimensional data can be employed using any number of well-established three-dimensional recording and displaying methods. Additionally, the three-dimensional representation can be displayed using the display device depicted in FIG. 28 in order to produce a holographic-type display. The display device comprises a pair of stereoscopic eyeglasses or spectacles 1080 which are worn by an observer 1082. The eyeglasses 1080 contain lenses which are either cross-polarized or which pass complementary colored light. In addition, a target 1084 is positioned on the eyeglass frame 1080. A color computer monitor 1086 and video camera or detector 1088 are provided in association with the eyeglasses 1080. The color monitor 1086 is used to display complementary-colored or cross-polarized stereoscopic image pairs 1090 of the three-dimensional representation. The video camera 1088 is used to track the target 1084 as the observer's head is moved. When the observer's head is moved to a different position, the video camera 1088 relays information either directly to the color monitor 1086 or to the color monitor 1086 through computer-related hardware. The information relayed by the video camera relates to the angle subtended by the target 1084 relative to the video camera 1088. The relayed information is then used to alter the angular disparity associated with the stereoscopic image pairs 1090 being displayed on the color monitor 1080 in quasi-realtime, so that the resulting display is adjusted to correlate with the movement of the observer's head and appears holographic to the observer.

Figure 39:
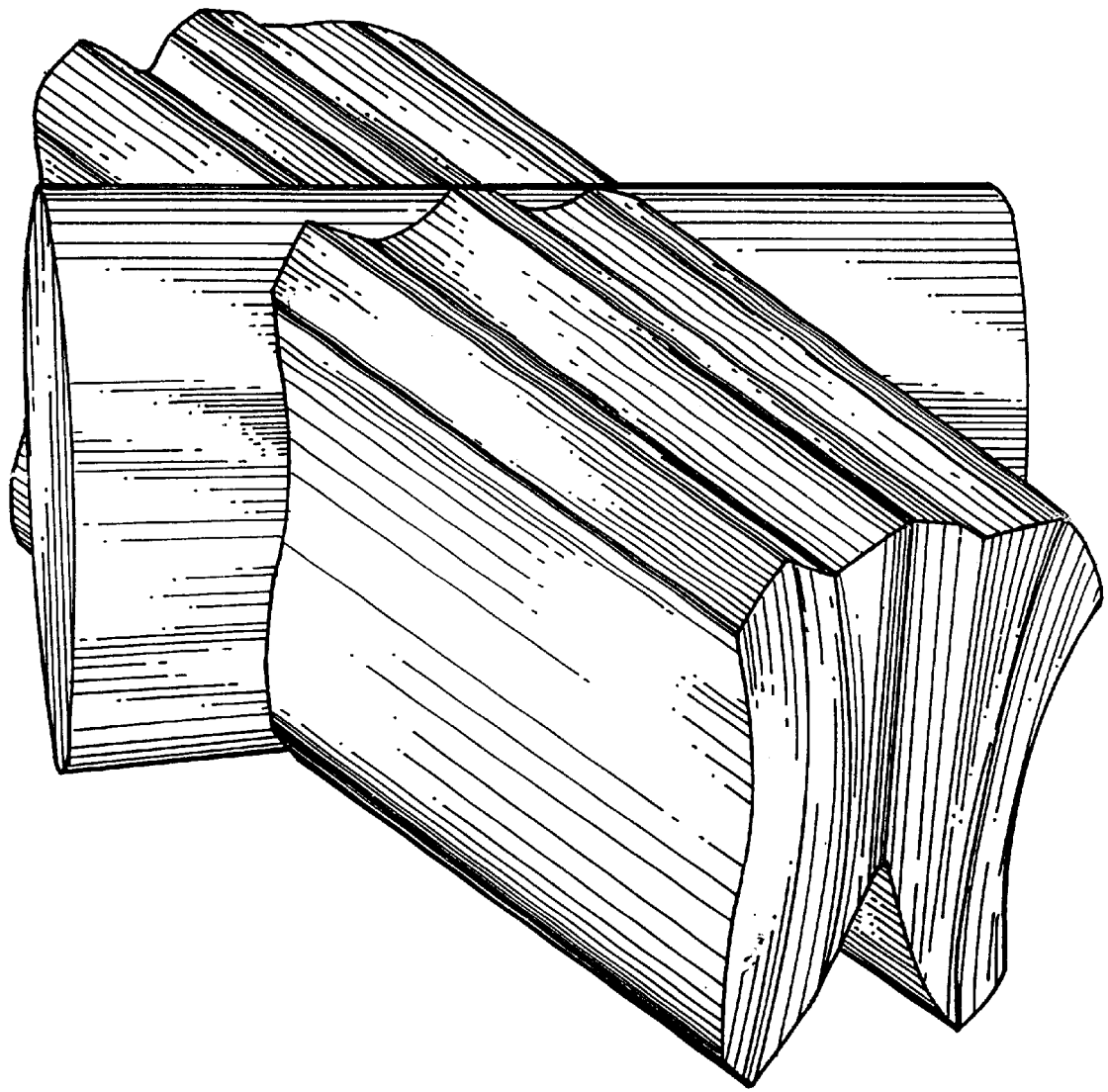
FIG. 39 is a schematic representation of a three-dimensional image of an object produced from a single pair of arbitrary two-dimensional images.

Instead of creating a slice image or a three-dimensional representation from one or more series of two-dimensional images, a nearly isotropic three-dimensional image can be created from a single pair of two-dimensional projections as depicted in FIG. 39. As shown, the two-dimensional images are combined and overlap to produce a three-dimensional image. Since only one two-dimensional image is utilized to reconstruct each slice image, the method depicted in FIG. 39 represents a completely degenerate case wherein the slice image is infinitely thick. When the slice image is infinitely thick, the slice image is indistinguishable from a conventional two-dimensional projection of a three-dimensional object.

Figure 32:
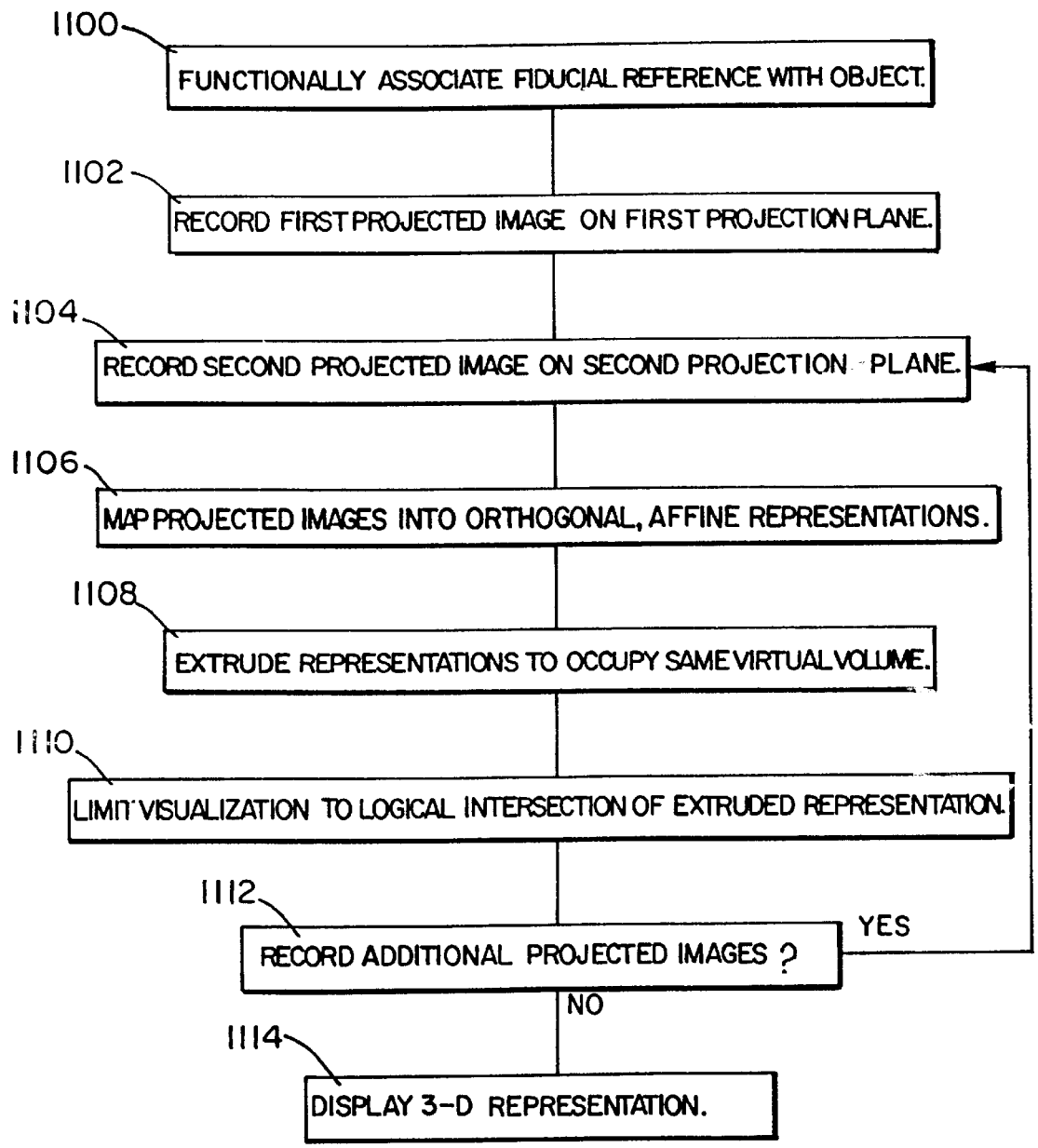
FIG. 32 is a flow chart showing the steps of a method for creating nearly isotropic three-dimensional images from a single pair of arbitrary two-dimensional images.

The steps of a method for producing a three-dimensional image of an object from a single pair of two-dimensional projections is shown in FIG. 32. At step 1100, a three-dimensional fiducial reference is functionally associated with an object of interest. The association need only be complete enough to permit the location of all of the details in the object to be determined relative to the position of the object. The fiducial reference must occupy a volume and be defined spatially such that a minimum of six points can be unequivocally generated and/or identified individually. For example, the object may be encased inside a cubic reference volume wherein the corners of adjacent faces are rendered identifiable by tiny, spherical fiducial markers.

A first projected image is then produced on a first projection plane at step 1102. The relative positions of the object, the radiation source, and the detector are then altered so that a second projected image can be recorded on a second projection plane at step 1104. The second projection plane must be selected so that it intersects the first projection plane at a known angle. However, for the resultant three-dimensional representation to be mathematically well conditioned, the angle should be or approach orthogonality.

At step 1106, a projective transformation of each projected image is performed to map the images of the fiducial reference on each face into an orthogonal, affine representation of the face. For example, when a cubic fiducial reference is used, the projective transformation amounts to converting the identifiable corners of the image of the fiducial reference corresponding to a projected face of the fiducial reference into a perfect square having the same dimensions as a face of the fiducial reference.

Each of the transformed projected images is then extruded, at step 1108, such that both projected images occupy the same virtual volume. The extrusion step is equivalent to the creation of a virtual volume having the same dimensions as the fiducial reference containing the sum of the transformed projected images. At step 1110, an optional non-linear filtering technique is used to limit visualization of the three-dimensional representation to the logical intersection of the transformed projected images.

The three-dimensional representation can be refined by optionally recording additional projected images. At step 1112, it is determined whether additional projected images are to be recorded. If additional projected images are desired, the process returns to step 1104. However, if additional projected images are not desired, the three-dimensional representation is displayed at step 1114.

Figure 33:
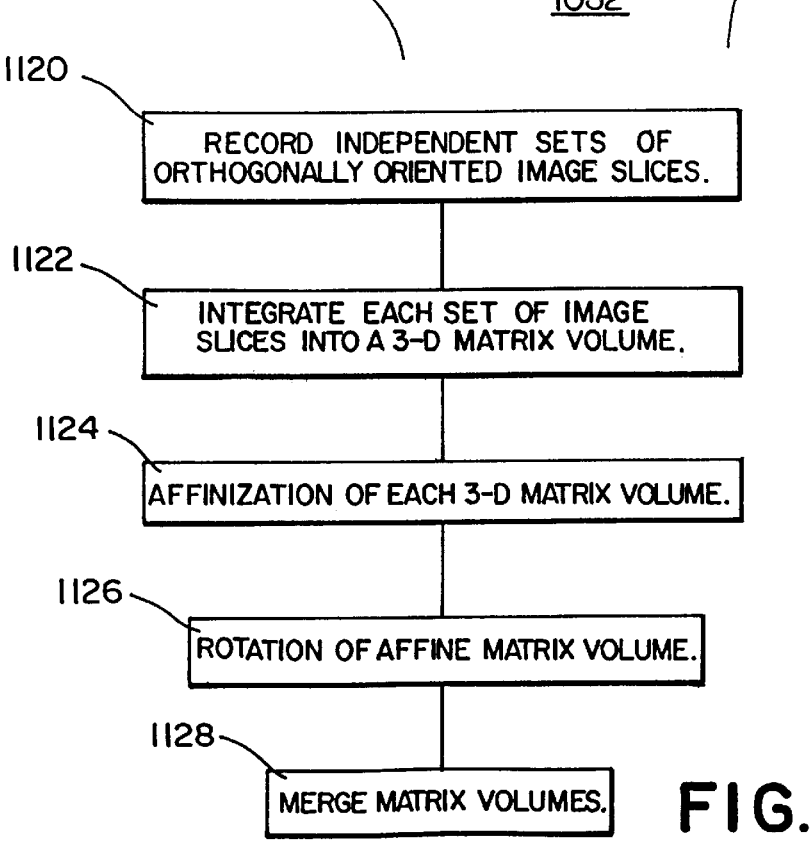
FIG. 33 is a flow chart showing the steps of a method for creating a three-dimensional image from two series of two-dimensional images.

The present invention also relates to a method for reducing distortions in the three-dimensional representation. Tomosynthesis uses two-dimensional image projections constrained within a limited range of angles relative to the irradiated object to produce a three-dimensional representation of the object. The limited range of angles precludes complete and uniform sampling of the object. This results in incomplete three-dimensional visualization of spatial relationships hidden in the resulting undersampled shadows or null spaces. Another limiting factor which interferes with artifact-free tomosynthetic reconstruction is the change in slice magnification with depth caused by the relative proximity of the source of radiation. These distortions can be reduced by merging independently generated sets of tomosynthetic image slices, as shown in FIG. 33.

At step 1120, a fiducial reference is functionally associated with the object and at least two independent sets of image slices are recorded. The angular disparity between the sets of image slices is noted. For example, the first set of image slices may comprise multiple anterior-posterior projections while the second set of image slices comprises multiple lateral projections. The sets of image slices are then integrated to create a first and a second three-dimensional tomosynthetic matrix volume at step 1122.

At step 1124, the resulting three-dimensional matrix volumes are affinized to counteract the effects of having a finite focal-object distance. Affinization is accomplished by first identifying the reference images of the appropriate reference markers of the fiducial reference. Once the reference images have been identified, the three-dimensional matrix volumes are shifted and scaled in order to correct for geometrical and surface imperfections. The transformation of the first three-dimensional matrix volumes is carried out in accordance with the following equation:

$$A'=CA$$

where A is the first three-dimensional matrix volume, A' is the shifted and scaled first three-dimensional matrix volume, and C is the affine correction matrix for the first three-dimensional matrix volume. The affine correction matrix C is determined by the number of slices comprising the three-dimensional matrix volume, the correlation angle (i.e., the greatest angle of the projection sequence in the range $$\left[-\frac{\pi}{4} \to \frac{\pi}{4}\right]$$

measured from an axis normal to the detector surface), and the correlation distance (i.e., the apex-to-apex distance created by the intersection of the most disparate projections of the sequence). The transformation of the second three-dimensional matrix volume is analogously determined in accordance with the following equation:

$$L'=DL$$

where L is the second three-dimensional matrix volume, L' is the shifted and scaled second three-dimensional matrix volume, and D is the affine correction matrix for the second three-dimensional matrix volume.

At step 1126, the second three-dimensional matrix volume is rotated by an angle $\phi$. The angle $\phi$ is defined as the angular disparity between the first and the second three-dimensional matrix volumes. Specifically, the shifted and scaled second three-dimensional matrix volume, L', is rotated in accordance with the following equation:

$$L''=R_\phi L'$$

where L" is the rotated, shifted, and scaled second three-dimensional matrix volume and $R_\phi$ is the rotational transform matrix.

The transformed matrix volumes, A' and L", are then merged using matrix averaging at step 1128. The matrix averaging is accomplished in accordance with the following equation:

$$M = \frac{1}{2}(A' + L'')$$

where M is the averaged matrix of the two component transformed matrix volumes, A' and L". Alternatively, a non-linear combination of the transformed matrix volumes, A' and L", is performed.

Figure 24:
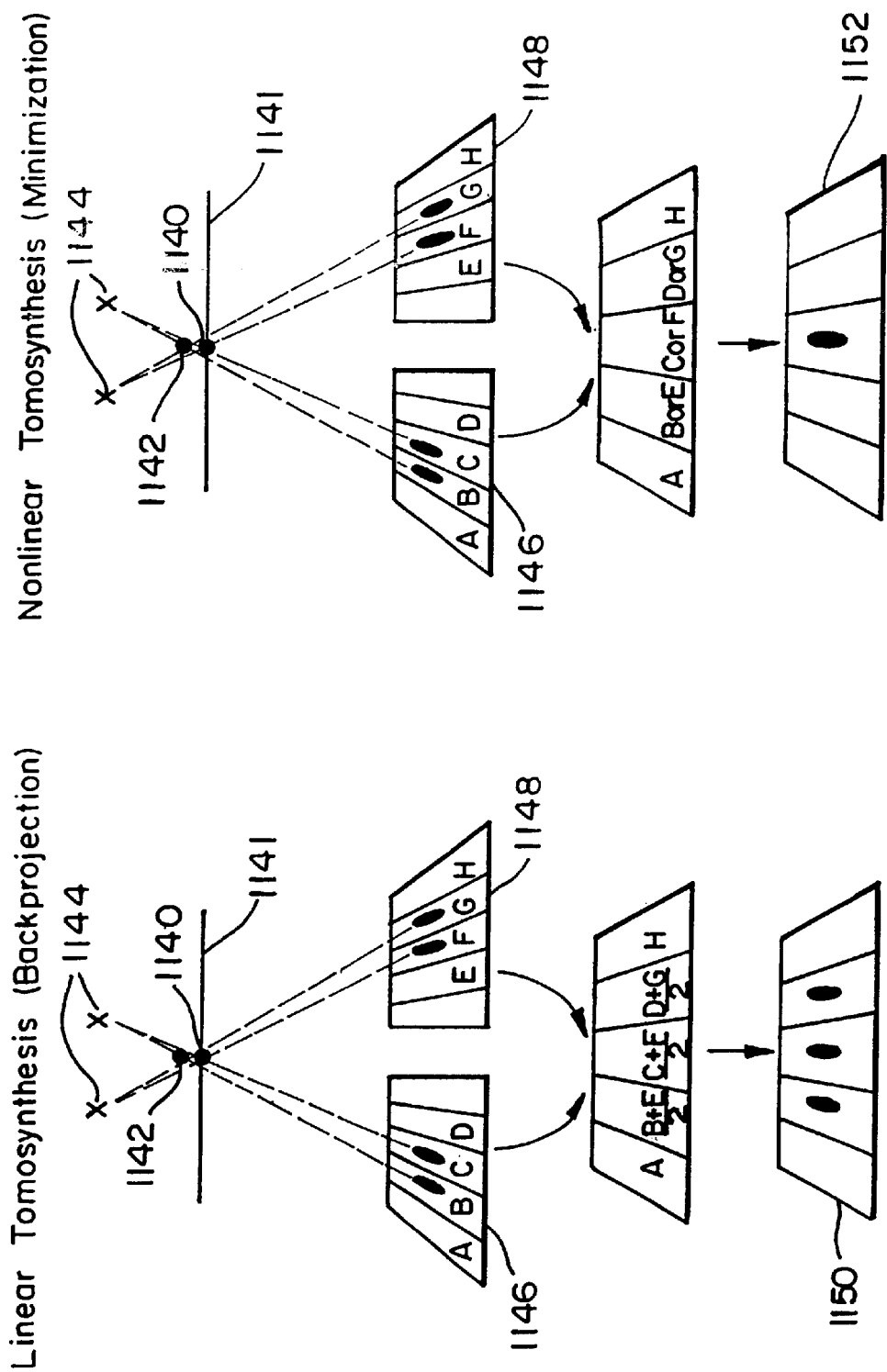
FIGS. 24 A and B are schematic representations of a linear tomosynthetic reconstruction and a non-linear tomosynthetic reconstruction in accordance with the present invention.

The present invention further relates to a method for generating tomosynthetic images optimized for a specific diagnostic task. A task-dependent method for tomosynthetic image reconstruction can be used to mitigate the effects of ringing artifacts from unregistered details located outside the focal plane of reconstruction, which are intrinsic to the tomosynthetic reconstruction process. The production and elimination of blurring artifacts is depicted schematically in FIG. 24. As shown, a first radiopaque object 1140 within the focal plane 1141 and a second radiopaque 1142 object above the focal plane are irradiated from two different source positions 1144 to produce two distinct data images. The first data image 1146 contains an image of the first radiopaque object 1140 at relative position C and an image of the second radiopaque object 1142 at relative position B. The second data image 1148 contains an image of the first radiopaque object 1140 at relative position F and an image of the second radiopaque object 1142 at relative position G. When a linear combination of the first and second data images is performed, the image intensity at the same relative position of both data images is averaged. For example, relative position B in one data image corresponds to relative position E in the other data image and, therefore, the corresponding relative position in the tomosynthetic image is assigned an intensity equal to the average of the intensity measured at relative position B and relative position E (i.e., (B+E)/2). As a result, the tomosynthetic image 1150 is marked by a blurring of the image produced by the first radiopaque object 1140. However, when a non-linear combination of the first and second data images is performed, both data images are compared and, for example, only the minimum intensity at each relative position is retained. For example, relative position B in one data image corresponds to relative position E in the other data image and, therefore, the corresponding relative position in the tomosynthetic image is assigned an intensity equal to the lesser of the intensities measured at relative position B and relative position E (i.e., B or E). As a result, the blurring shadows are eliminated from the tomosynthetic image 1152.

The non-linear tomosynthetic approach in accordance with the present invention is beneficial when, for example, physicians want to know with relative assurance whether a lesion or tumor has encroached into a vital organ. When viewing a linear tomosynthetic reconstruction of the general region in three dimensions, the ringing artifacts tend to blur the interface between the lesion or tumor and the surrounding tissues. However, since tumors are typically more dense than the tissues that are at risk of invasion, the non-linear tomosynthetic reconstruction can be employed such that only the relatively radiopaque tumor structures of interest are retained in the reconstructed image. Similarly, a different non-linear operator could be used such that only relatively radiolucent structures of interest are retained in the reconstructed image to determine whether a lytic process is occurring in relatively radiopaque tissues.

The use of non-linear operators to reduce the affects of ringing artifacts is effective because images of many structures of radiographic interest have projection patterns determined almost entirely by discrete variations in mass or thickness of relatively uniform materials. Under these conditions, changes in radiographic appearance map closely with simple changes in either material thickness or density. In other words, complicating attributes associated with visual images, such as specular reflections, diverse energy-dependent (e.g., color) differences, etc., do not contribute significantly to many diagnostic radiographic applications. This simplification assures that many tissues can be identified easily by their position in a monotonic range of X-ray attenuations. Accordingly, selection of only projections yielding maximum or minimum attenuations when performing tomosynthetic reconstructions derived from such structures assures that resulting image slices yield results characterized by only extremes of a potential continuum of display options. Such displays make sense when the diagnostic task is more concerned with specificity (i.e., a low likelihood of mistaking an artifact for a diagnostic signal) than sensitivity (i.e., a low likelihood of missing a diagnostic signal).

Figure 23:
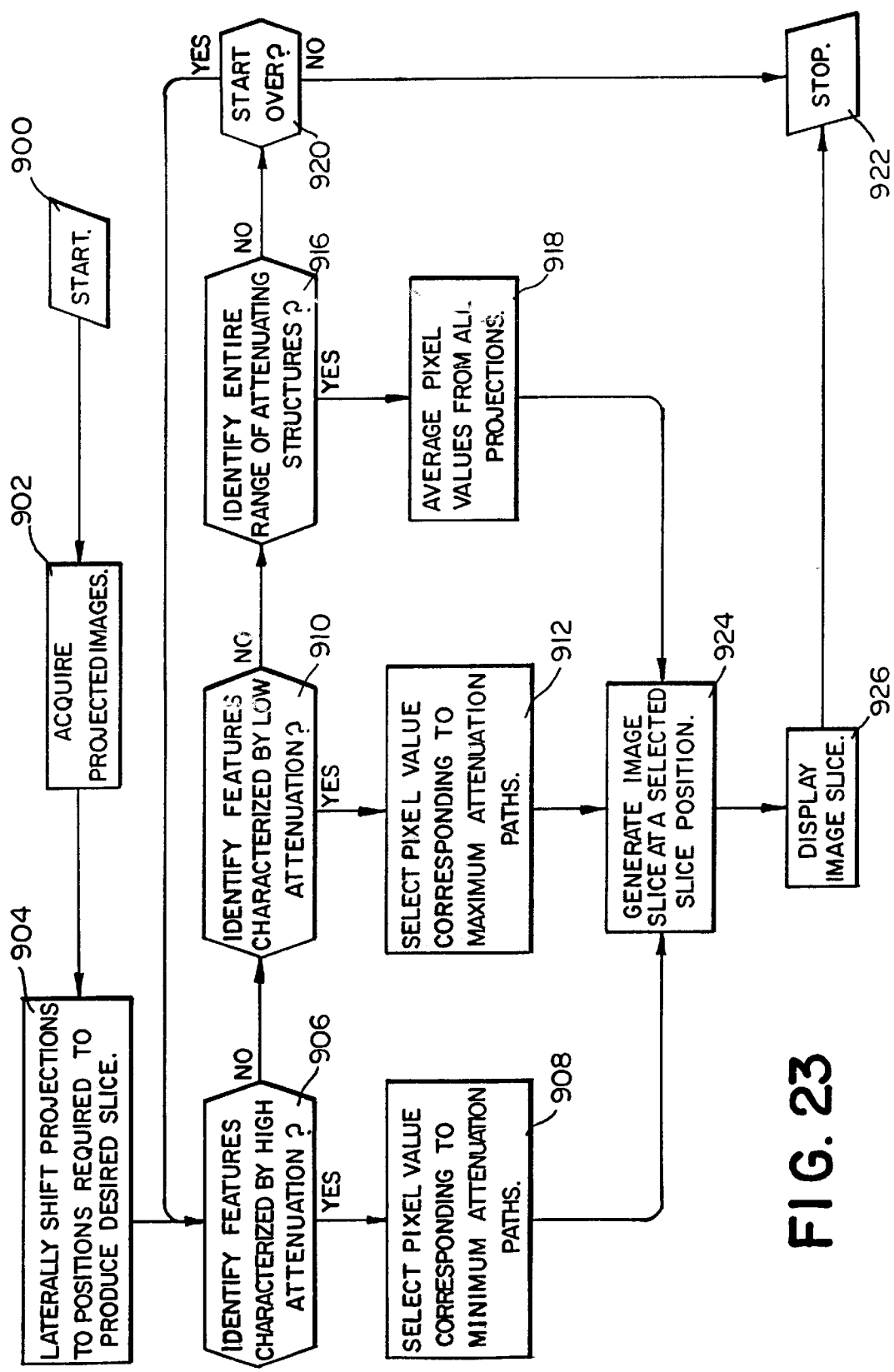
FIG. 23 is a flow chart showing the steps involved in a method for task-dependent tomosynthetic image reconstruction in accordance with the present invention.

A method for task-dependent tomosynthetic image reconstruction is depicted in the flow chart of FIG. 23. The method begins at step 900 and proceeds to step 902 where a series of projected images are acquired. In one embodiment, the projected images are acquired in the same manner already described in connection with steps 49–55 of FIG. 2. At step 904, the projected images are shifted laterally, in the plane of the projection, by amounts required to produce a desired tomosynthetic slice where all the images are then superimposed, in a manner identical to the method described in connection with steps 60 and 65 of FIG. 2.

Once the projected images have been acquired and appropriately shifted, the type and degree of task-dependent processing is chosen. At step 906, it is determined whether only those features characterized by a relatively high attenuation are to be unequivocally identified. If only features having a high attenuation are to be identified, a pixel value corresponding to a desired minimum attenuation is selected. The selected pixel value is used as a minimum threshold value whereby each projected image is analyzed, pixel by pixel, and all pixels having an associated attenuation value below the selected pixel value are disregarded when an image slice is generated.

If however, at step 906, it is determined that features having a low attenuation are to be identified or that the entire range of attenuating structures are to be identified, then it is determined at step 910 whether only features characterized by a relatively low attenuation are to be unequivocally identified. If only features having a low attenuation are to be identified, a pixel value corresponding to a desired maximum attenuation is selected. The selected pixel value is used as a maximum threshold value whereby each projected image is analyzed, pixel by pixel, and all pixels having an associated attenuation value above the selected pixel value are disregarded when an image slice is generated.

If it is determined at step 910 that features having a low attenuation are not to be identified or that the entire range of attenuating structures are to be identified, then it is determined at step 916 whether an unbiased estimate of the three-dimensional configuration of the entire range of attenuating structures is to be identified. If the entire range of attenuating structures is to be identified, then conventional tomosynthesis is performed at step 918, whereby the attenuation values from all of the projected images are averaged.

If the features having a high attenuation, the features having a low attenuation, and the features covering the entire range of attenuations are not to be identified, then it is determined at step 920 whether the user desires to restart the selection of features to be identified. If the user wants to restart the identification process, then the method returns to step 906. If the user decides not to restart the identification process, then the method ends at step 922.

Once it has been determined which features are to be identified, then an image slice is generated at a selected slice position at step 924. The process for generating the image slice at step 924 is essentially the same as discussed previously in connection with step 90 of FIG. 2. However, when only features having either a high attenuation or a low attenuation are to be identified, the image generation process is performed only on the non-linearly selected images, instead of on all of the projected images as initially acquired. Once the image slice has been generated, the image slice is displayed at step 926 and the method ends at step 922.

In another aspect of the present invention, a method is provided for determining temporal changes in three-dimensions. The method enables two or more sets of image data collected at different times to be compared by adjusting the recorded sets of image data for arbitrary changes in the vantage points from which the image data were recorded. The method takes advantage of the fact that a single three-dimensional object will present a variety of different two-dimensional projection patterns, depending on the object's orientation to the projection system. Most of this variety is caused by the fact that a three-dimensional structure is being collapsed into a single two-dimensional image by the projection system. Limiting projection options to only two-dimensional slices precludes this source of variation. The result is a much reduced search space for appropriate registration of the images required to accomplish volumetrically meaningful subtraction.

Figure 25:
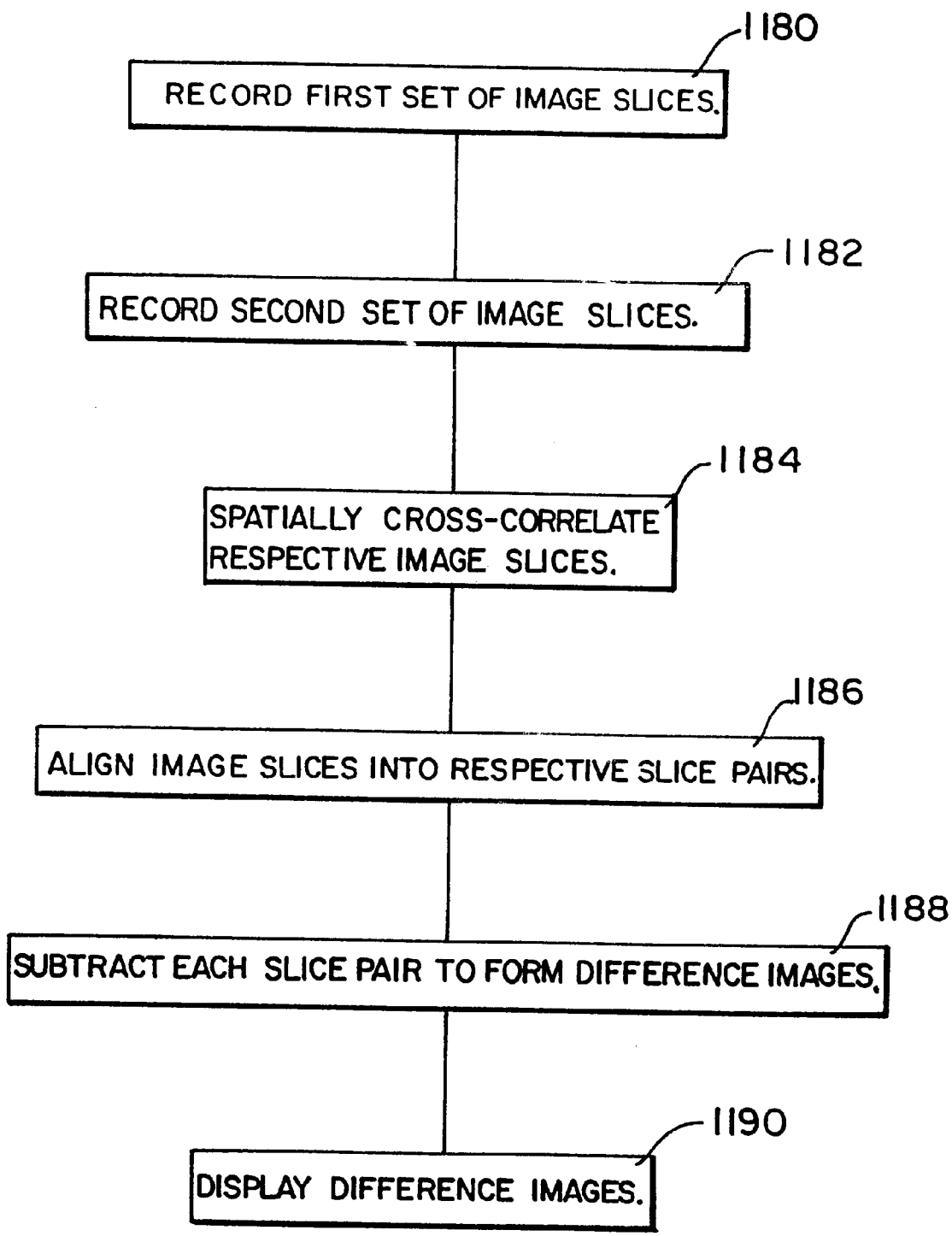
FIG. 25 is a flow chart showing the steps involved in a method for determining temporal changes in accordance with the present invention.

A flow chart showing the steps involved in the method for determining temporal changes in three-dimensions of the present invention is depicted in FIG. 25. A first set of image slices is generated at step 1180. After the desired time period to be assessed for changes has passed, the object is positioned in roughly the same position as it was when the first set of image slices was produced and a second set of image slices is generated, at step 1182, using a similar exposure protocol.

At step 1184, the first set of image slices is spatially cross-correlated with the second set of image slices. The cross-correlation is accomplished by individually comparing each image slice comprising the first set of image slices with the individual image slices comprising the second set of image slices. The comparison is performed in order to determine which image slice in the second set of image slices corresponds to a slice through the object at approximately the same relative position through the object as that of the image slice of the first set of image slices to which the comparison is being made.

After each of the image slices in the first set of image slices is correlated to an image slice in the second set of image slices, each of the correlated pairs of image slices are individually aligned at step 1186. The alignment is performed in order to maximize the associated cross-correlations by maximizing the overlap between the image slices comprising the correlated pairs of image slices. The cross-correlations are maximized by shifting the image slices relative to one another until the projected image of the object on one image slice is optimally aligned with the projected image of the object on the other image slice. Once each correlated pair of image slices has been aligned, the image slices from one set of image slices is subtracted from the image slices from the other set of image slices at step 1188 to form a set of difference images.

At step 1190, the difference images are displayed. The difference images can be presented as a series of individual differences corresponding to various different slice positions. Alternatively, the individual difference images can be integrated to yield a composite difference representing a three-dimensional image of the temporal changes associated with the selected object.

The present invention further relates to a source comparator and a method for matching radiation sources for use in quantitative radiology. Meaningful quantitative comparisons of different image data can be made only when the radiation source or sources used to record the image data is very nearly unchanged. However, conventional radiation sources produce radiation that varies with changes in tube potential, beam filtration, beam orientation with respect to the radiation target, tube current, and distance from the focal spot. The source comparator and method of the present invention enable the radiation output from one radiation source to be matched to that of another radiation source or to that of the same radiation source at a different time.

Figure 26:
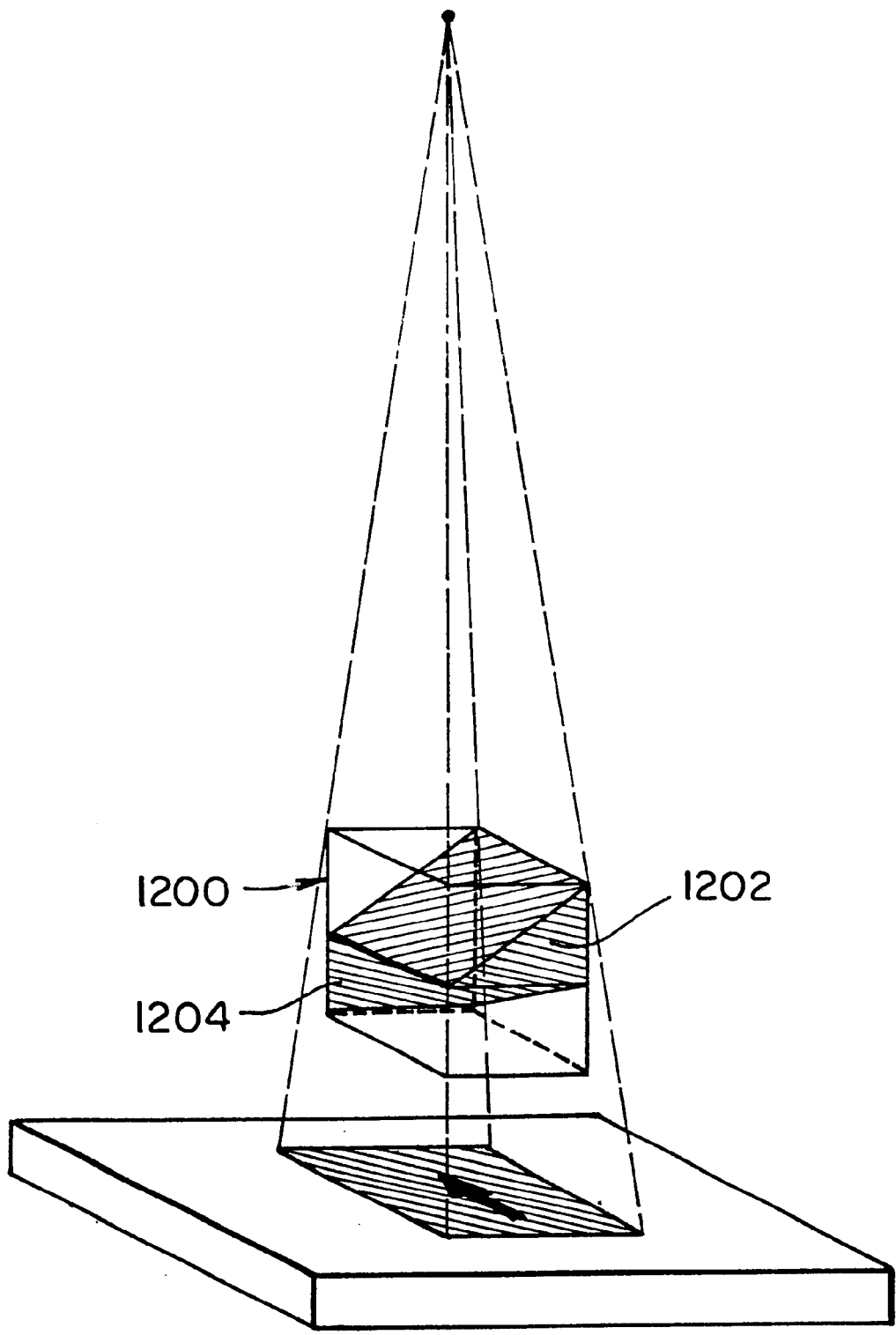
FIG. 26 is a schematic representation of a source comparator used for matching X-ray sources.

The source comparator 1200 for matching radiation sources in accordance with the present invention is depicted in FIG. 26. The source comparator 1200 comprises two wedges or five-sided polyhedrons, 1202 and 1204, of equal dimension having a rectangular base and two right-triangular faces. The triangular faces lie in parallel planes at opposite edges of the base such that the triangular faces are oriented as mirror images of each other. As a result, each wedge, 1202 and 1204, has a tapered edge and provides a uniformly increasing thickness from the tapered edge in a direction parallel to the plane of the base and perpendicular to the tapered edge. The wedges, 1202 and 1204, are arranged with the base of one wedge 1202 adjacent to the base of the other wedge 1204 such that the tapered edges of the two wedges are at adjacent edges of the base. One wedge is formed from a uniform high attenuation material while the other wedge is formed from a uniform low attenuation material to differentially attenuate the relative proportion of high and low energy photons in the output from the radiation source. Accordingly, when the source comparator 1200 is irradiated from a radiation source directed perpendicularly to the bases of the wedges, the resulting image will be a quadrilateral having an intensity gradient that varies uniformly in a single direction with the angle of the gradient being determined by the distribution of high and low energy photons in the output from the radiation source.

Figure 27:
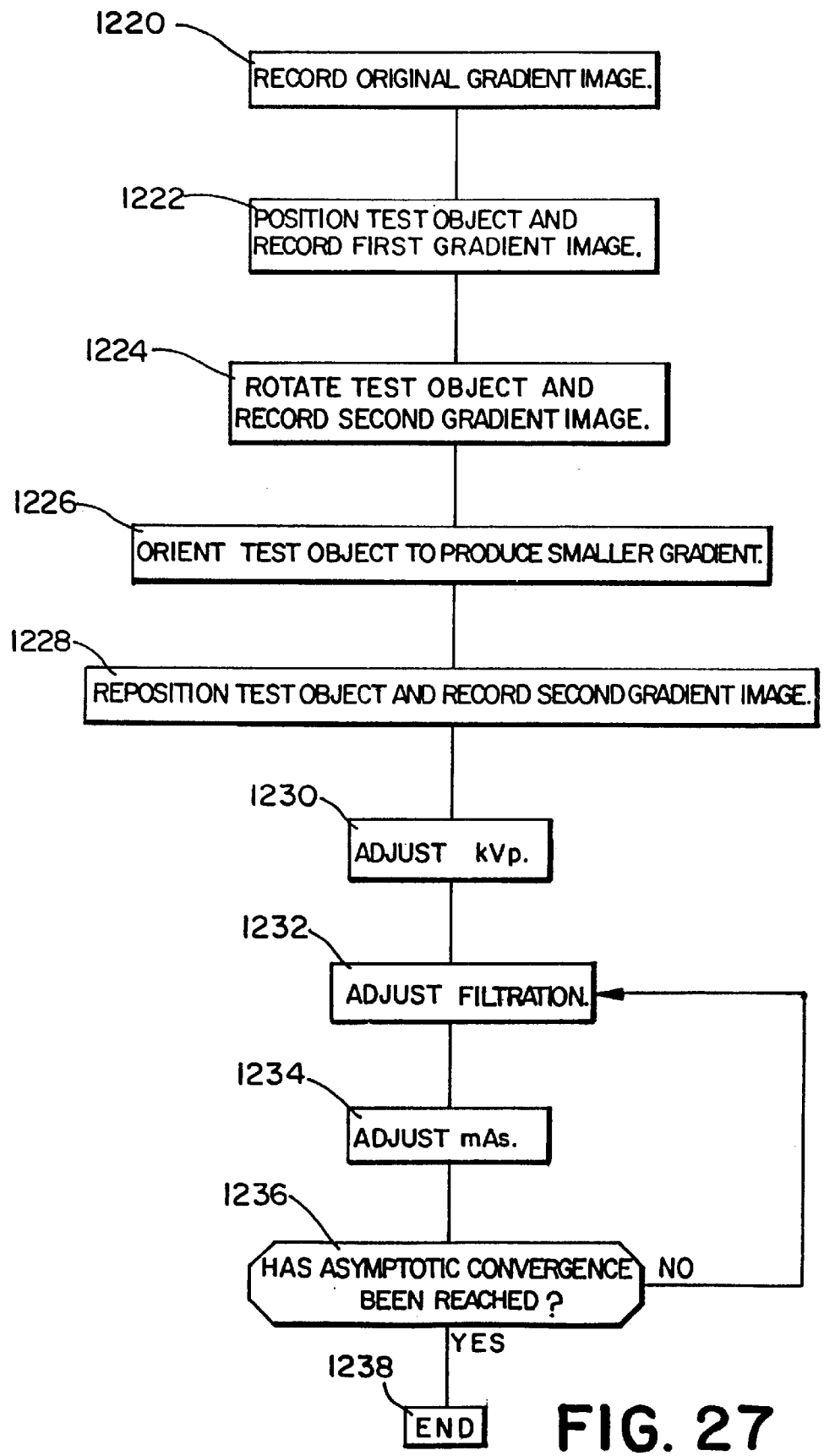
FIG. 27 is a flow chart showing the steps of a method for using the source comparator of FIG. 26.

The source comparator 1200 of FIG. 26 is used in the method of matching radiation sources in accordance with the present invention as shown in FIG. 27. At step 1220, the source comparator is positioned between a radiation source and a detector. An original gradient image is then recorded by exposing the source comparator to radiation from the radiation source at the source settings to be used for recording a first set of data images. The first set of data images is then recorded.

When a second set of data images is to be recorded, the source settings for the radiation source to be used to record the second set of data images are adjusted to match the settings used for recording the first set of data images. At step 1222, the source comparator is positioned between the radiation source and the detector and a first gradient image is recorded. The source comparator is then rotated perpendicularly to the detector by an angle of 180° and a second gradient image recorded at step 1224. The first and second gradient images are compared and the source comparator oriented to produce the smaller gradient at step 1226. By so doing, it is assured that the source comparator bears the same relative relationship to the radiation source for both sets of data and, thereby, eliminates the potential for confounding the data by spatial variations in the cross-sectional intensity of the output from the radiation source.

The individual settings on the radiation source are then iteratively adjusted. At step 1230, the beam energy is matched by adjusting the kVp on the radiation source so that the measured gradient value approaches the gradient value of the original gradient image. The beam quality is then matched at step 1232 by adjusting the filtration of the radiation source so that the angle of the maximum gradient relative to the edge of the source comparator approaches that of the original gradient image. The beam exposures are then estimated by integrating the detector response across a fixed region of the source comparator and matched at step 1234 by adjusting the mAs of the radiation source so that the exposure approaches that of the original gradient image. At step 1236 it is determined whether the gradient image is substantially the same as the original gradient image. If the two images are significantly different, the beam energy, beam quality, and exposure are readjusted. If, however, asymptotic convergence has been reached and the two gradient images are substantially the same, the radiation sources are matched and the process ends at step 1238. Once the radiation sources have been matched, the second set of data images can be recorded and quantitatively compared to the first set of data images.

In the embodiment shown in FIG. 19, the source 627 is an unconstrained point source and the detector 631 is completely constrained relative to the object 621. Accordingly, the system has three degrees of freedom (two translational and one displacement for the radiation source 627 relative to the object 621 and detector 631). A beam collimator 647 can be positioned between the source 627 and the object 621 to collimate the radiation from the source 627. The detector 631 comprises a primary imager 632 and a secondary imager 634 positioned a known distance below the primary imager 632. In one embodiment, both the primary and secondary imagers, 632 and 634, are CCD detectors. The fiducial reference 622 comprises a radiopaque shield 633 with a ring-shaped aperture 636 of known size positioned between the primary imager 632 and the secondary imager 634.

Radiation from the source 627 passes through collimator 647, irradiates object 621, and produces an object image on the primary imager 632. In addition, radiation from the source 627 which impinges upon the radiopaque shield 633 passes through the aperture 636 to produce a ring-shaped reference image of the aperture 636 on the secondary imager 634. Since the secondary imager 634 is not used to record object images, the secondary imager 634 can be a low quality imager such as a low resolution CCD. Alternatively, a lower surface of the primary imager 632 can be coated with a phosphorescent material 635, so that radiation impinging upon the primary imager 632 causes the phosphorescent material 635 to phosphoresce. The phosphorescence passes through the aperture 636 to produce the reference image on the secondary imager 634.

In operation, the reference image produced using the system depicted in FIG. 19 can be used to determine the position of the source 627 relative to the object 621 and the detector 631. A circle, or ellipse, is fitted to the projected reference image. By fitting a circle, or ellipse, to the reference image, the effect of dead areas and/or poor resolution of the secondary imager 634 can be eliminated by averaging. The position of the center of the fitted circle, or ellipse, relative to the known center of the aperture 636 is determined. The angle a of a central ray 637 radiating from the source 627 relative to the object 621 and the detector 631 can then be determined. In addition, the length of the minor diameter of the projected reference image is determined and compared to the known diameter of the aperture 636 to provide a relative magnification factor. The relative magnification factor can then be used to determine the distance of the source 627 from the object 621.

The center of the fitted circle can be determined as follows. A pixel or point on the secondary imager 634 that lies within the fitted circle is selected as a seed point. For convenience, the center pixel of the secondary imager 634 can be selected, since the center point will typically lie within the fitted circle. A point R is determined by propagating from the seed point towards the right until the fitted circle is intersected. Similarly, a point L is determined by propagating from the seed point towards the left until the fitted circle is intersected. For each pixel along the arc L-R, the average of the number of pixels traversed by propagating from that pixel upwardly until the fitted circle is intersected and the number of pixels traversed by propagating from that pixel downwardly until the fitted circle is intersected is determined. Any statistical outliers from the averages can be discarded and the average of the remaining values calculated. This average represents the row address of the fitted circle's center. To obtain the column address, the entire reference image is rotated by 90° and the process is repeated. The row address and column address together represent the position of the center of the fitted circle.

Although the above embodiments have been described in relation to projected images of objects produced using X-rays, the present invention is equally applicable to images produced using a variety of technologies, such as visible light, ultrasound, or electron microscopy images. Specifically, intermediate voltage electron microscope (IVEM) images can be used to provide quantitative three-dimensional ultrastructural information. Further, the present invention can also be used to reconstruct three-dimensional images of objects which either emit or scatter radiation.

When IVEM images are used, the present invention allows cellular changes to be detected and quantified in an efficient and cost-effective manner. Quantitation of three-dimensional structure facilitates comparison with other quantitative techniques, such as biochemical analysis. For example, increases in the Golgi apparatus in cells accumulating abnormal amounts of cholesterol can be measured and correlated with biochemically measured increases in cellular cholesterol.

When photographic images are used, it is possible to create a true three-dimensional model of a diffusely illuminated fixed scene from any number of arbitrary camera positions and angles. The resulting three-dimensional image permits inverse engineering of structural sizes and shapes, and may be expressed as a series of topographic slices or as a projective model that can be manipulated interactively. This capability is particularly useful in retrofitting existing structures or quantifying three-dimensional attributes using non-invasive methods. In addition, the present invention can be applied to construct topological images of geological structures by recording images of the structure created by the sun.

EXAMPLES

Representative lumpectomy specimens containing cancer from human breasts were radiographed using a digital mammographic machine (Delta 16, Instrumentarium, Inc.). Exposure parameters were regulated by an automatic exposure control mechanism built into the unit. Seven distinct projections of each specimen were made using a swing arm containing the tube head that swept across each specimen in a single arched path. This resulted in mammographic projections having angular disparities of 15, 10, 5, 0, −5, −10, and −15 degrees from vertical. These data were processed to yield a series of tomosynthetic slices distributed throughout the breast tissues in three ways: 1) conventional linear summation of all seven appropriately shifted projections (FIG. 29), 2) identical linear summation augmented by the application of an interactive deconvolution filter known to minimize tomographic blur (FIG. 30), and 3) a nonlinear tomosynthetic reconstruction scheme based on selection of only the projection(s) yeilding the minimum brightness at each pixel (FIG. 31). Notice the lack of "ringing" artifacts caused by the wire used to locate the lesion in FIG. 31 corresponding to the nonlinear reconstruction method. Five board-certified radiologists compared tomographic displays of these tissues produced from all three methods and ranked them in terms of their perceived interpretability with regard to cancer recognition and relative freedom from apparent tomosynthetic artifacts. A related exercise involved having a different set of eight observers estimate the relative depths of a series of seven holes bored in a solid Lucite block exposed under comparable conditions.

All five radiologists preferred the nonlinearly generated tomosynthetic mammograms over those produced conventionally (with or without subsequent blurring via interactive deconvolution). A similar statistically significant result ($p<0.05$) was produced when the performance of the hole-depth experiment was objectively determined.

This approach is very efficient: it is simpler to implement than conventional tomosynthetic back-projection methods; and it produces sharp-appearing images that do not require additional computationally intensive inverse filtering or interative deconvolution schemes. Therefore, it has the potential for implementation with full-field digital mammograms using only modest computer processing resources that lie well within the current state of the art. For certain tasks that are unduly compromised by tomosynthetic blurring, a simple nonlinear tomosynthetic reconstruction algorithm may improve diagnostic performance over the status quo with no increase in cost or complexity.

Although the above discussion has centered around computed tomography, it will be appreciated by those skilled in the art that the present invention is useful for other three-dimensional imaging modalities. For example, the present invention is also intended to relate to images obtained using magnetic resonance imaging (MRI), single photon emission computed tomography (SPECT), positron emission tomography (PET), conventional tomography, tomosynthesis, and tuned-aperture computed tomography (TACT), as well as microscopic methods including confocal optical schemes.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A system for synthesizing an image slice, consisting of an array of pixels with each pixel having an associated value, of a selected object at a selected slice position through the selected object from a plurality of projected radiographic images of the selected object comprising:

a. at least one radiographic recorder for recording radiographic images of the selected object, each radiographic image consisting of an array of pixels with each pixel having an associated value;

b. at least one source of radiation for irradiating the selected object to enable projected radiographic images of the selected object to be recorded on the radiographic recorder; and c. an image synthesizer for synthesizing the image slice from selected projections of the projected radiographic images, wherein the image synthesizer comprises means for assigning a value to each pixel of the image slice equal to a maximum value of the attenuation values of a set of corresponding pixels in the projected images.

2. A system for synthesizing an image slice, consisting of an array of pixels with each pixel having an associated value, of a selected object at a selected slice position through the selected object from a plurality of projected radiographic images of the selected object comprising:

a. at least one radiographic recorder for recording radiographic images of the selected object, each radiographic image consisting of an array of pixels with each pixel having an associated value;

b. at least one source of radiation for irradiating the selected object to enable projected radiographic images of the selected object to be recorded on the radiographic recorder; and c. an image synthesizer for synthesizing the image slice from selected projections of the projected radiographic images, wherein the image synthesizer comprises means for assigning a value to each pixel of the image slice equal to a minimum value of the attenuation values of a set of corresponding pixels in the projected images.

3. A method for synthesizing an image of a selected object at a selected slice position through the selected object from a plurality of projected optical images of the selected object comprising the steps of:

a. providing at least one optical recorder for recording optical images of the selected object;

b. identifying at least one fiducial reference in fixed position relative to the selected object, the fiducial reference defining a first and a second object point;

c. providing at least one source of radiation for irradiating the selected object to enable projected optical images of the selected object and the fiducial reference to be recorded on the optical recorder;

d. recording projected optical images of the selected object and the fiducial reference at different relative positions between (1) the source of radiation, (2) the selected object and the fiducial reference, and (3) the optical recorder, each projected optical image comprising a first reference image associated with the first object point and a second reference image associated with the second object point;

e. recording for each optical image a distance from the optical recorder to the object and an angular orientation of the optical recorder with respect to the object;

f. transforming the projected optical images, using the distance data, to render each of the projected optical images at a common magnification;

g. selecting representative transformed optical image and projectively transforming the remaining transformed optical images to lie along the direction of the representative optical image;

h. shifting each of the transformed optical images by an amount sufficient to align the images of the first point;

i. determining a projected reference image distance for each projected optical image, the projected reference image distance corresponding to a distance between the first and the second object points;

j. calibrating the distances between transformed optical images based on the projected reference image distance and the angular orientation; and k. remapping the transformed optical images based on calibrated distances.

4. The method according to claim 3 wherein the remapping step is performed using the first object point as a common point of superposition.

5. The method according to claim 3 wherein the remapping step specifies the relative position of transformed projections along a direction perpendicular to the selected representative transformation.

6. The method according to claim 3 wherein the at least optical recorder has a first and a second apertures, and wherein a first set of the projected optical images is recorded using the first aperture and a second set of the projected optical images is recorded using the second aperture.

* * * * *